US006790616B1

(12) United States Patent
Moribe et al.

(10) Patent No.: US 6,790,616 B1
(45) Date of Patent: Sep. 14, 2004

(54) METHOD FOR TYPING OF HLA CLASS I ALLELES

(75) Inventors: Toyoki Moribe, Settsu (JP); Toshihiko Kaneshige, Settsu (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/856,662

(22) PCT Filed: Oct. 7, 1999

(86) PCT No.: PCT/JP99/05527

§ 371 (c)(1),
(2), (4) Date: May 24, 2001

(87) PCT Pub. No.: WO00/31295

PCT Pub. Date: Jun. 2, 2000

(30) Foreign Application Priority Data

Nov. 26, 1998 (JP) .......................... 10-335151

(51) Int. Cl.[7] .......................... C12Q 1/68; C12Q 1/00; C12P 19/34; C07H 21/00
(52) U.S. Cl. .......................... 435/6; 435/4; 435/91.2; 536/23.1; 536/24.3; 536/24.33
(58) Field of Search .............................. 435/4, 6, 91.2; 536/23.1, 24.3, 24.33

(56) References Cited

FOREIGN PATENT DOCUMENTS

| WO | 98/26091 | 6/1998 |
|---|---|---|
| WO | WO 9826091 A2 | 6/1998 |

OTHER PUBLICATIONS

Kox et al. (Journal of Clinical Microbiology (1996) vol. 34, pp. 2117–2120).*
Olejnik et al. (Nucleic Acids Research (1998) vol. 26, pp. 3572–3576).*
Kawai et al (Human Immunology (1994) vol. 41, pp. 121–126).*
GenBank Accession No. X97645 (Dec. 2, 1996).*
Tokunaga et al. (Human Immunology (1996) vol. 47, abstract P561, p. 103).*
Zammatteo et al. (Analytical Biochemistry (1996) vol. 236, pp. 85–94).*

(List continued on next page.)

*Primary Examiner*—Marjorie Moran
(74) *Attorney, Agent, or Firm*—Birch, Stewart, Kolasch & Birch, LLP

(57) ABSTRACT

This invention provides a method, a kit and a reagent for typing of the HLA class I alleles. Explaining concretely, a single HLA class I antigen or allele is determined by combining PCR amplification using a primer pair which can amplify all HLA-A alleles, all HLA-B alleles or all HLA-C alleles, or which is specific to the common sequence to alleles of the specific group consisting of the specific HLA-A alleles or the specific HLA-B alleles, with reverse hybridization analysis using DNA probes capable of specifically hybridizing with the sequence of al least a specific HLA-A allele, at least a specific HLA-B allele or at least a specific HLA-C allele, which are covalently immobilized on wells of microtiter plates.

12 Claims, 6 Drawing Sheets

OTHER PUBLICATIONS

Bannai et al., *Nichijo Shinryo to Ketsueki*, vol. 5, No. 10, pp. 1269–1274 (Abstract only).
Janer et al., *Genomics*, vol. 51, No. 1, pp. 35–44 (1998).
Moribe et al., *Human Immunology*, vol. 60, pp. 539–549 (1999).
Moribe et al., *Proceedings of the Japanese Society for Immunology*, vol. 28, p. 122 (1998) (No translation).
Moribe et al., *Proceedings of the Japanese Society for Immunology*, vol. 28, p. 122 (1998) (English translation).
M, Sakauchi et al., "HLA and Desease–2.; Progress in HLA Examination Method (in Japanese)", Nichijo shinryo to ketsueki (1995) vol. 5,No. 10, p. 1269–1274.

Marta Janer et al., "The human major histocompatibility complex:42, 221 bp of genomic sequence,high–density sequence–tagged site map, evolution, and polymorphism for HLA class I", Genomics (1998) vol. 51, No. 1,p. 35–44.

Moribe Toyoki et al., "Rapid HLA class I DNA typing using microtiter plate–reverse hybridization assay (MRHA) by simple thermoregulation;high–resoution subtyping of the HLA–A2 and–B40 antigen groups", Human Immunology (Jun. 1999) vol. 60,p539–549.

* cited by examiner

Closed box (■) : positive signal
Opened box (□) : negative signal

Figure 2

HLA-B40 (*High Resolution*)

| Well number | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| HLA-B allele / SSO probes | BL222A | BL34 | BL35 | BL4 | BL5 | BL24 | BL25 | BL512T | BL37 | BL39 | BL41 | BL50 | BL56 | BL57 | BL409T |
| B*4001 | ■ | □ | □ | ■ | □ | ■ | □ | ■ | □ | □ | □ | □ | ■ | □ | □ |
| B*4002 | ■ | □ | □ | ■ | □ | ■ | □ | □ | ■ | □ | □ | □ | ■ | □ | □ |
| B*4003 | ■ | □ | □ | ■ | □ | ■ | □ | □ | □ | □ | □ | □ | □ | ■ | □ |
| B*4009 | ■ | □ | □ | ■ | □ | ■ | □ | □ | ■ | □ | □ | □ | □ | □ | ■ |
| B*4004 | ■ | □ | □ | ■ | □ | ■ | □ | □ | □ | □ | ■ | □ | ■ | □ | □ |
| B*4006 | ■ | □ | □ | ■ | □ | ■ | □ | □ | □ | □ | □ | ■ | □ | □ | □ |
| B*4702 | ■ | □ | □ | ■ | □ | ■ | □ | □ | □ | □ | ■ | □ | □ | □ | □ |
| B*4007 | ■ | □ | ■ | □ | ■ | □ | ■ | □ | □ | □ | □ | □ | ■ | □ | □ |
| B*4008 | ■ | □ | ■ | □ | ■ | □ | ■ | ■ | □ | □ | □ | □ | ■ | □ | □ |
| B*4701 | ■ | □ | ■ | □ | ■ | □ | □ | □ | □ | □ | □ | □ | ■ | □ | □ |

Closed box (■) : positive signal

Opened box (□) : negative signal

Closed box (■) : positive signal
Opened box (□) : negative signal

Figure 4

HLA-B (*Medium Resolution*)

| Well number | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| HLA-B antigen | HLA-B allele | BL36 | BL37 | BL38 | BL39R | BL40 | BL41 | BL42 | BL77 | BL78 | BL79 | BL1 | BL9 | BL3 | BL4 | BL10 | BL11 | BL272A | BL226G | BL263T | BL34 | BL527A | BL538CG+BL538G | BL570GT |

Closed box (■): positive signal     Opened box (□): negative signal

Figure 5

| HLA-B antigen | HLA-B allele | Well number | | | | | | | | | | | | | | | | | | | | | | |
|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| | | SSO probes | | | | | | | | | | | | | | | | | | | | | | |
| | | BL36 | BL37 | BL38 | BL39R | BL40 | BL41 | BL42 | BL77 | BL78 | BL79 | BL1 | BL9 | BL3 | BL4 | BL10 | BL11 | BL272A | BL226G | BL263T | BL34 | BL527A | BL538CG+BL538G | BL570GT |

| HLA-B antigen | HLA-B allele |
|---|---|
| B61 | B*4004 |
| B13 | B*1301 |
| B44 | B*4402/05 |
| B44 | B*4403 |
| B48 | B*4802 |
| B17 | B*5702 |
| B17 | B*5701/03/5801/03 |
| B62,75 | B*1502/25 |
| B62 | B*1520 |
| B77 | B*1513 |
| B35,75 | B*1521/3511 |
| B35 | B*3508 |
| B35 | B*3501/02/03/04/06/07/09/10/12/13 |
| B51 | B*5104 |
| B44 | B*4406 |
| B53 | B*5301 |
| B44 | B*4404 |
| B50 | B*5001 |
| B45 | B*4501 |
| B49 | B*4901 |
| B63 | B*1516 |
| B41 | B*4101 |
| B61 | B*4006 |
| B73 | B*7301 |
| B13 | B*1302 |
| B56 | B*5601 |
| B62 | B*1504 |
| B52 | B*5201 |
| B13 | B*1303 |
| B78 | B*7801/02 |
| B51 | B*5101/02 |
| B51 | B*5103 |
| B51 | B*5105 |
| B55 | B*5501 |
| B55 | B*5502 |
| B39 | B*3906 |
| B59 | B*5901 |
| B54 | B*5401 |
| B17 | B*5802 |
| B14 | B*1401/02 |
| B37 | B*3701 |

Closed box (■) : positive signal    Opened box (□) : negative signal

Closed box (■) : positive signal
Opened box (□) : negative signal

METHOD FOR TYPING OF HLA CLASS I ALLELES

This application is the national phase under 35 U.S.C. §371 of PCT International Application No. PCT/JP99/05527 which has an International filing date of Oct. 7, 1999, which designated the United States of America and was published in English.

TECHNICAL FIELD

HLA (Human Leukocyte Antigen) that is Human major histocompatibility antigen, is expressed on membranes of imuunocompetent cells, presents processed peptides derived from exogenous and endogenous antigens to T lymphocytes, and functions as a marker to recognize self and non-self. The present invention relates to a method, a reagent and a kit for typing of the HLA class I alleles. This invention is especially useful for judgement of compatibility between a donor and a recipient in organ transplantation, and for association analysis between the HLA class I genes and various types of diseases in the clinical and medical field. This invention enables us to easily automate and mechanize detection and determination of the HLA class I alleles.

BACKGROUND OF ART

Typing of the HLA antigens has been mainly performed by the serological method using human alloantibodies. By using the specific antibodies to each HLA antigen which are contained in cord blood or serum from subjects who have frequently undergone blood transfusion, complement-mediated cytotoxicity is caused in the antigen-antibody reaction. It changes permeability of positive cell membranes to take an eosinic pigment into the cell, resulting in being detected as colored and expanding cells with a microscope. It is possible to type HLA-A, HLA-B and HLA-C antigens belonging to HLA class I, and HLA-DR and HLA-DQ antigens belonging to HLA class II by this method. However, this method has problems in terms of collection, quality control and supply of the specific antibodies. Furthermore, the survival rate of cells is utilized as an indicator for judgement in this method. Therefore, poor conditions of subjects, for example, a low survival rate of cells caused by disease or influence by passage of time after blood collection, lead to decrease of credibility for results of testing.

In recent years, a development of molecular biotechnology has enabled us to analyze the region of genes encoding the HLA antigens. That has clarified the correspondence between the HLA antigens and the sequences of the HLA genes. This means it has been possible to identify the HLA antigen type by analyzing the specific sequences of the HLA genes (DNA typing). Especially, PCR (polymerase chain reaction) method which can high-sensitively detect a slight change of sequences isutilized to type the HLA-DR, -DQ, or -DP genes belonging to HLA class II. Several PCR-based typing methods for HLA class II DNA such as PCR-SSOP (Sequence-Specific Oligonucleotide Probe) method, PCR-RFLP (Restriction Fragment Length Polymorphism) method, PCR-SSP (Sequence-Specific Primers) method and PCR-SSCP (Single Strand Conformation Polymorphism) method have been developed. In all these methods, the gene region to analyze is amplified by the PCR method and then the variable region in the sequences of the amplified products is analyzed by combination with another methods in order to distinguish the genotype. The HLA class II DNA typing method makes it possible to classify the HLA type at the allele level in addition to classification by the classical serological method using human alloantisera.

Development of the PCR based-method for BLA class I DNA typing is delayed remarkably, comparing with HLA class II typing. The reasons are as follows: (1) While almost all the class II gene mutations (gene substitutions), including those which reflect the specificity of antigens, concentrate in the region of the exon 2, the class I gene mutations are interspersed among the regions of the exons 2 and 3, or the exon 4. (2) The HLA class I genes, including non-classical genes (HLA-E, -F and -G) and pseudogenes (HLA-H, -J, -K and -L), are highly homologous among them.

To date, several HLA class I DNA typing methods have been reported. However, all these methods require complicated manipulation, strict reaction condition and skill. Those are not suitable for handling a large number of samples and offer only low resolution HLA typing. Furthermore, the typing methods for each gene are not standardized.

Disclosure of Invention

The purpose of this invention is to solve problems of the manipulation of HLA class I locus antigen typing by the classical serological method, and to prodive a method, a kit and a reagent for classifing the subtype of the HLA class I antigens at the allele level (allele typing), which has not been distinguished by the classical method. Furthermore, the aim of this invention is to provide a method for typing of the HLA class I alleles which can automate and machanize easily.

As a result of intensive studies for these subjects, the inventors have established primers which can amplify all the HLA-A alleles, all the HLA-B alleles or all the HLA-C alleles and specific primers to the common sequences among all alleles in the group consisting of the specific HLA-A alleles or the specific HLA-B alleles. The inventors have established probes which can specifically hybridize with the sequence of at least one specific HLA-A allele, at least one specific BLA-B allele or at least one specific HLA-C allele. The inventors have found out that it is possible to distinguish the HLA class I antigen or allele, by hybridizing the PCR amplified products derived from the specific HLA class I allele or the specific group with the DNA probes described above which are immobilized on wells of microtiter plates, adding an enzyme-conjugate which can specifically bond to a label of the amplified products at the same time as or after the hybridization, and adding a chromogenic substrate, a luminescent substrate or a fluorescent substrate to the mixture, to detect as signals whether or not the amplified products are hybridized with the immobilized DNA probes. Thus, they have accomplished this invention.

The main embodiment of this invention is a method for typing of HLA class I alleles, which comprises the following steps from (a) to (d).

(a) A step, using HLA class I gene or nucleic acids containing their fragment for a template,
  (1) To non-selectively amplify all HLA-A alleles, all HLA-B alleles or all HLA-C alleles by a PCR method using a primer pair which can amplify all the HLA-A alleles, all the HLA-B alleles or all the HLA-C alleles, or
  (2) To selectively amplify a specific group consisting of specific HLA-A alleles or specific HLA-B alleles by a PCR method using a primer pair which is specific to the common sequence to alleles of the specific group consisting of the specific HLA-A alleles or the specific HLA-B alleles, (b) A step to add the above products amplified by the PCR method to wells of microtiter plates, wherein each well is modified with a carboxyl group to covalently immobilize amino-modified DNA probes which can specifically hybridize with the sequence of at least one specific HLA-A allele, at least one specific HLA-B allele or at least one specific HLA-C allele, and to hybridize the amplified products with the immobilized DNA probes, wherein the DNA probes are selected depending on the above amplified specific HLA class I gene or group;

(c) A step to detect as signals whether or not the amplified products are hybridized with the immobilized probes; and (d) A step to determine the type of the HLA class I allele based on the signal pattern detected at the step (c) according to the Typing Table.

The PCR amplification of the target gene at the step (a), can be classified into 2 steps. One is a step to non-selectively amplify all the HLA-A alleles, all the HLA-B alleles or all the HLA-C alleles by the PCR method using a primer pair which can amplify all the HLA-A alleles, all the HLA-B alleles or all the HLA-C alleles. The other is a step to selectively amplify the specific group consisting of the specific HLA-A allele group or the specific HLA-B allele group by the PCR method using a primer pair which is specific to the common sequences to alleles of the specific group consisting of the specific HLA-A alleles or the specific HLA-B alleles. At the former step, PCR primers are designed to be specific to the common sequences, which are within the region of all alleles belonging to the HLA-A allele, the HLA-B allele or the HLA-C allele, or ahead and behind the region. At the latter step, PCR primers are designed to be specific to the common sequences to all alleles included in the specific group in order to amplify the specific group. When the specific group is selectively amplified in the presence of some groups, the primers described above don't need to be used for both a sense primer and an anti sense primer of a primer pair corresponding to the specific group. It is possible to use the specific primer to the specific group for one of primers and the specific primer to all the groups for the other. The latter step can be performed according to the reference described by the inventors (Tissue Antigens 1997, Vol.50, 535–545). A method to selectively amplify alleles encoding the HLA-A2 antigen or the HLA-B40 antigen as a group is disclosed in the present description.

At the step (a), the PCR-amplified products derived from the allele belonging to the HLA-A alleles, the HLA-B alleles or the HLA-C alleles, or from the specific group, are produced. But it is not possible to distinguish the type of the HLA class I allele at the step. The hybridization reaction at the step (b) using the specific DNA probes is applied to the following steps.

The Typing Table at the step (d) is made using signal patterns obtained by hybridizing the PCR amplified products from samples whose HLA class I antigen types or allele types are known, with DNA probes which can specifically hybridize with the sequence of at least one specific HLA class I allele. Persons skilled in the art can make easily the Typing Table. As the Typing Table, FIGS. 1 to 6 can be referred. If someone wants to use DNA probes, which are not described in this description, another Typing Table can be used. The Typing Table is made from signal patterns obtained by hybridizing the PCR amplified products from samples whose HLA class I antigen types or allele types are known, with another DNA probe. As described above, persons skilled in the art can also make easily these Typing Tables. It should be considered that each sample has the HLA class I allele type in a homozygous or heterozygous state, when the HLA class I allele type is distinguished according to the Typing Tables.

In a preferable embodiment, the PCR method at the step (a) is performed by using a primer pair in which at least one of them is labeled, in order to detect whether or not the amplified products hybridize with immobilized DNA probes as signals at the step (c) described above. In the other embodiment, the above PCR can be performed by using 4 kinds of deoxyribonucleotide triphosphate (dNTP) in which at least one of them is labeled. As a substance used for labeling, a radioisotopic substance, or a non-radioisotopic substance such as a biotin or a digoxigenin, can be utilized.

In a preferable embodiment, at the step (b) or (c) described above, the hybridization of the products amplified by the PCR method with the immobilized DNA probe is performed by addiing an enzyme-conjugate which can specifically bond to a label of the amplified products is added at the same time as hybridization or after, and the amplified products hybridizing with the immobilized DNA probe is detected as signals by adding a chromogenic substrate, a luminescent substrate or a fluorescent substrate which can specifically react with the enzyme. When a peroxidase-conjugated streptavidin is used as an enzyme-conjugate, the signal can be immediately detected after washing by adding an enzyme-conjugate at the same time as hybridization.

In a preferable embodiment, at least one of a primer pair at the step (a) described above is biotinylated, and an enzyme-conjugate which can specifically bond to the biotinylated label at the step (b) or (c) is an enzyme-conjugated streptavidin, for example, a peroxydase-conjugated streptavidin or an alkaline phosphatase-conjugated streptavidin.

In a preferable embodiment, the hybridization of the products amplified by the PCR method with immobilized DNA probes is performed in a solution containing formamide at the step (b) described above. The formamide concentration of the solution described above (hybridization buffer) is from 5% to 30%, and from 10% to 25% as a preferable concentration. The concentration can be changed according to the sequence, the length and the type of the used DNA probe. The most preferable formamide concentration is about 20%.

In a preferable embodiment, the hybridization at the step (b) is performed in a solution containing formamide at the temperature of the 37° C. The preferable temperature is from 32° C. to 42° C. The temperature can be changed according to the sequence, the length and the type of the used DNA probe as mentioned above for the formamide concentration. The most desirable temperature is about 37° C. Hybridization is usually performed at comparatively high temperature, at about 65° C., to improve the specificity. By using the solution containing formamide, the reaction can be performed at low temperature, at about 37° C.

In a preferable embodiment, when the solution containing formamide is used for the hybridization at the step (b) described above, the temperature for washing after hybridization of the amplified products by the PCR method with immobilized DNA probes and/or after binding a label of the amplified products with an enzyme-conjugate is performed at room temperature. Namely, washing can be performed at low temperaure like room temperature as by using the solution containing formamide, as well as the above hybridization.

The amino-modified DNA which can specifically hybridize with at least one specific HLA-A allele, used at the step (b) in this invention, can be selected from the group consisting of A98T (SEQ ID No.:1), A98A (SEQ ID No.:2), A160A (SEQ ID No.:3), A239A (SEQ ID No.:4), A238A (SEQ ID No.:5), A240T (SEQ ID No.:6), A257TC (SEQ ID No.:7), A259AC (SEQ ID No.:8), A270T (SEQ ID No.:9), A282C (SEQ ID No.:10), A290T (SEQ ID No.:11), A299T (SEQ ID No.:12), A302G (SEQ ID No.:13), A355G (SEQ ID No.:14), A362TA (SEQ ID No.:15), A362TT (SEQ ID No.:16), A368A (SEQ ID No.:17), A368G (SEQ ID No.:18), A368T (SEQ ID No.:19), A402G (SEQ ID No.:20), A423T (SEQ ID No.:21), A448C (SEQ ID No.:22), A485A (SEQ ID No.:23), A524G (SEQ ID No.:24), A526T (SEQ ID No.:25), A527A (SEQ ID No.:26), A538CG (SEQ ID No.:27), A539A (SEQ ID No.:28), A539T (SEQ ID No.:29), A555T (SEQ ID No.:30), A559G (SEQ ID No.:31), A570CG (SEQ ID No.:32), A570GT (SEQ ID No.:33), A779A (SEQ ID No.:34), A843A (SEQ ID No.:35), A34 (SEQ ID No.:100), A282CT (SEQ ID No.:101), A290TR (SEQ ID No.:102), A302GR (SEQ ID No.:103), A414A (SEQ ID No.:104), A468T (SEQ ID No.:105), A489A (SEQ ID No.:106), A502C (SEQ ID No.:107), A538TG (SEQ ID No.:108) and complementary strands thereof.

The amino-modified DNA probe which can specifically hybridize with at 10 least one specific HLA-B allele can be selected from the group consisting of BL1 (SEQ ID No.:36), BL3 (SEQ ID No.:37), BL4 (SEQ ID No.:38), BL5 (SEQ ID No.:39), BL9 (SEQ ID No.:40), BL10 (SEQ ID No.:41), BL11 (SEQ ID No.:42), BL24 (SEQ ID No.:43), BL25 (SEQ ID No.:44), BL34 (SEQ ID No.:45), BL35 (SEQ ID No.:46), BL36 (SEQ ID No.:47), BL37 (SEQ ID No.:48), BL38 (SEQ ID No.:49), BL39 (SEQ ID No.:50), BL40 (SEQ ID No.:51), BL41 (SEQ ID No.:52), BL42 (SEQ ID No.:53), BL56 (SEQ ID No.:54), BL57 (SEQ ID No.:55), BL78 (SEQ ID No.:56), BL79 (SEQ ID No.:57), BL222A (SEQ ID No.:58), BL272GA (SEQ ID No.:59), BL226G (SEQ ID No.:60), BL292G (SEQ ID No.:61), BL292T (SEQ ID No.:62), BL361G (SEQ ID No.:63), BL409T (SEQ ID No.:64), BL512T (SEQ ID No.:65), BL538CG (SEQ ID No.:66), BL538G (SEQ ID No.:67), BL39R (SEQ ID No.:109), BL50 (SEQ ID No.:110), BL77 (SEQ ID No.:111), BL272A (SEQ ID No.:112), BL263T (SEQ ID No.:113), BL527A (SEQ ID No.:114), BL570GT (SEQ ID No.:115) and complementary strands thereof.

The amino-modified DNA probe which can specifically hybridize with at least one specific HLA-C allele can be selected from the group consisting of CC (SEQ ID No.:68), A-12 (SEQ ID No.:69), A-2 (SEQ ID No.:70), A-3 (SEQ ID No.:71), A-4 (SEQ ID No.:72), A-54 (SEQ ID No.:73), B-1 (SEQ ID No.:74), B-2 (SEQ ID No.:75), C-12 (SEQ ID No.:76), C-24 (SEQ ID No.:77), C-33 (SEQ ID No.:78), C-43 (SEQ ID No.:79), 134-g (SEQ ID No.:80), 134-A2 (SEQ ID No.:81), 353TCA1 (SEQ ID No.:82), 343A (SEQ ID No.:83), RA-2 (SEQ ID No.:116), RA-41 (SEQ ID No.:117), RB-28 (SEQ ID No.:118), 201g1 (SEQ ID No.:119), C206gR (SEQ ID No.:120), R341A (SEQ ID No.:121), R343g3 (SEQ ID No.:122), 353TCC (SEQ ID No.:123), 361T1 (SEQ ID No.:124), 361T368g (SEQ ID No.:125), 361T368T1 (SEQ ID No.:126), 369C (SEQ ID No.:127), 387g1 (SEQ ID No.:128), 526AC2 (SEQ ID No.:129), 538gAC (SEQ ID No.: 130) and complementary strands thereof.

This invention also comprises the DNA probe itself (from SEQ ID No.: 1 to SEQ ID No.:83 and from SEQ ID No.:100 to SEQ ID No.:130) which can specifically hybridize with at least one specific HLA-A allele, at least one specific HLA-B allele or at least one specific HLA-C allele for using the method for distinguishing the HLA class I allele type.

Both an amino-modified DNA probe and an unmodified DNA probe can be used. However, when the probe is covalently immobilized on wells of carboxylate-modified microtiter plates, the amino-modified probe must be used. Some bases can be deleted from or added to the end of the DNA probe within the range that the DNA probe can specifically hybridize with at least one specific HLA-A allele, at least one specific HLA-B allele or at least one specific HLA-C allele, namely, within the range that the DNA probe can keep the original specificity of hybridization. Accordingly, the DNA probes in this invention also comprise DNA probes wtherein some bases are deleted from or added to the nucleic acid sequence from SEQ ID No.:1 to SEQ ID No.:83 and SEQ ID No.:100 to SEQ ID No.:130 within the range described above.

The primers which can amplify all the HLA-A alleles, all the HLA-B alleles or all the HLA-C alleles at the step (a) in this invention, can be selected from the group consisting of CGA011 (SEQ ID No.:90), CGA012 (SEQ ID No.:91), AIn3-66C (SEQ ID No.:92), 5BCIn37-34C (SEQ ID No.:96), 5BCIn37-24g (SEQ ID No.:97) and 5BCIn37-34g2 (SEQ ID No.:99). The primer which is specific to the common sequence to alleles of the specific group consisting of the specific HLA-A alleles or the specific HLA-B alleles, can be selected from A2-5T (SEQ ID No.:84), A3-273T (SEQ ID No.:85), A4-8C (SEQ ID No.:86), A4-254G (SEQ ID No.:87), BASF-1 (SEQ ID No.:88), and BASR-1 (SEQ ID No.:89). This invention comprises the primer itself described above (from SEQ ID No.:88 to SEQ ID No.:92, from SEQ ID No.:96 to SEQ ID No.:97 and SEQ ID No.:99), used for the method to type the HLA class I alleles.

Novel HLA-A alleles, HLA-B alleles and HLA-C alleles have been discovered. In the report of the WHO (World Health Organization) Nomenclature Committee for the HLA system, 82, 186, and 42 of alleles have been assigned for the HLA-A, -B and -C loci, respectively, at March 1997. This invention can discriminate all these alleles. Furthermore, the method shown in this invention, together with an optional, easy-performed improvement, such as adding extra DNA probes or primers, can cope with discrimination of alleles which may be discovered and enrolled in the future.

This invention can provide a kit and a reagent for typing of the HLA class I alleles described in this description. Furthermore, this invention can provide a kit and a reagent which comprise the DNA probes and the primers described in this description. For example, the kit can comprises a solution containing the primers (from SEQ ID No.:84 to SEQ ID No.:92, from SEQ ID No.:96 to SEQ ID No.:97 and SEQ ID No.:99) which is disclosed in this invention, PCR buffer solution, which may be concentrated solution, dNTPs, thermostable DNA polymerase, the DNA probes (from SEQ ID No.:84 to SEQ ID No.:92, from SEQ ID No.:96 to SEQ ID No.:97 and SEQ ID No.:99) which is disclosed in this invention or a microtiter plate on whose wells the DNA probes are covalently immobilized, a denature solution, a hybridization buffer, a washing solution and an instruction for the kit which includes the Typing Tables. The primer described above can optionally be labeled with a radioisotopic or non-radioisotopic substance. The primers can form a primer pair. The solution containing the primer can be freeze-dried. When the primer is not labeled, at least one of four kinds of dNTPs must be labeled. When a non-radioisotopic substance is used as a label, an enzyme-conjugate solution, a chromogenic reagent including a chromogenic substrate and a chromogenic solution, a luminescent reagent or a fluorescent reagent, a stop solution and so on can be added as a component in the kit. Furthermore, a component such as guanidine thiocyanate buffer for isolation of genome DNAs, can be optionally added in the kit to the degree promoting enforcement of this invention.

BRIEF DESCRIPTION OF FIGURES

FIG. 2 indicates a Typing Table showing the reaction pattern between samples which the HLA-B40 allele type is known and DNA probes in the present invention. Each name of DNA probes is shown on the top in the Figure, and each type of the HLA-B40 alleles is shown on the left side in the Figure. Closed square and Open square mean a positive and a negative reaction, respectively.

FIGS. 4 and 5 indicate Typing Tables showing the reaction pattern between samples which the HLA-B antigen and allele type is known, and DNA probes in the present invention. Each name of DNA probes is shown on the top in the Figures, and each type of the HLA-B antigens and alleles is shown on the left side in the Figures. Closed square and Open square mean a positive and a negative reaction, respectively.

THE BEST MODE FOR CARRYING OUT THE INVENTION

Figure 1:
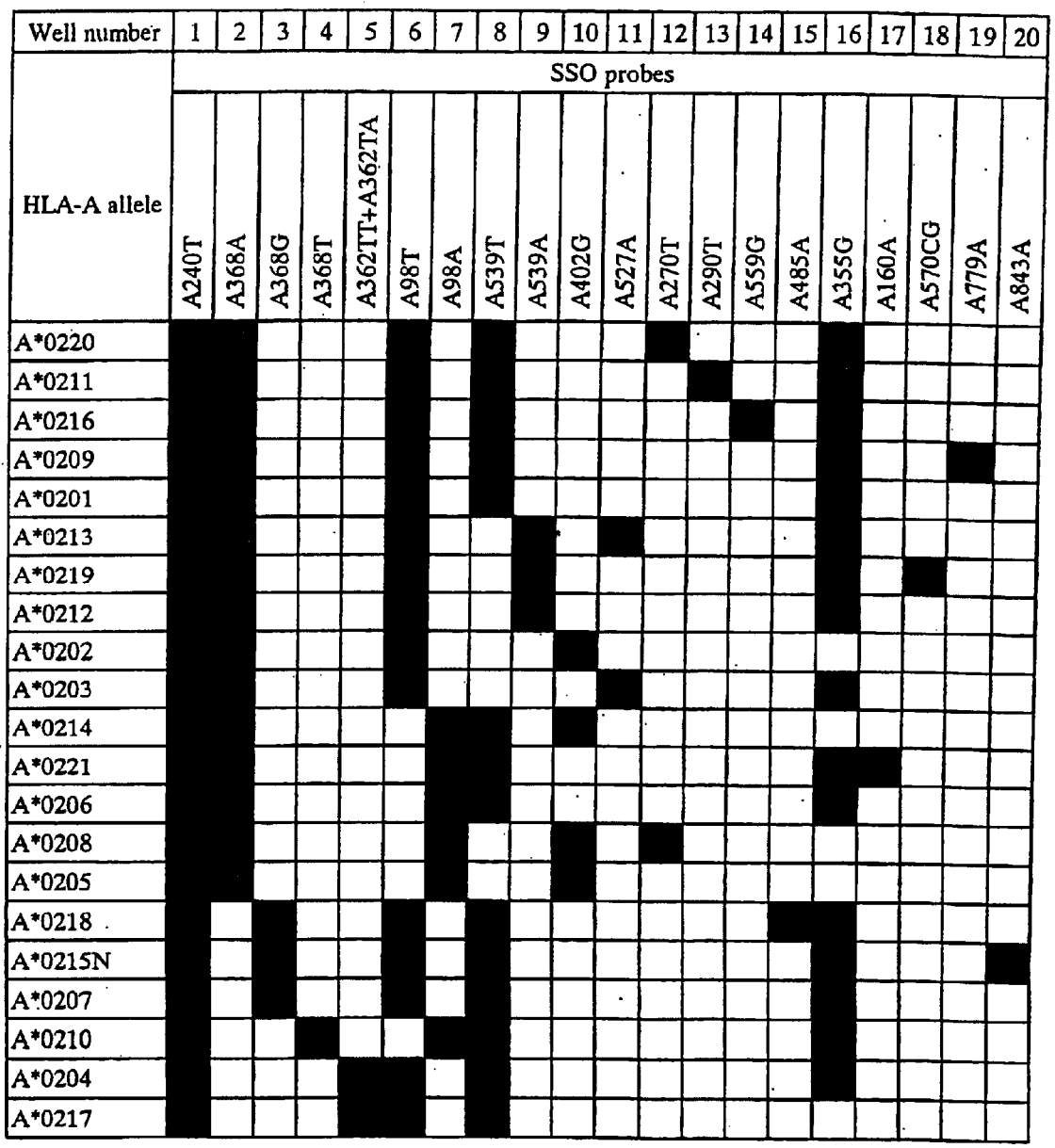
FIG. 1 indicates a Typing Table showing the reaction pattern between samples which the HLA-A2 allele type is known and DNA probes in the present invention. Each name of DNA probes is shown on the top in the Figure, and each type of the HLA-A2 alleles is shown on the left side in the Figure. Closed square and Open square mean a positive and a negative reaction, respectively.

The strategy of this invention described above is explained in more detail.

The typing method in this invention can be explained, dividing into the following 6 steps.

1) Extraction of chromosome(genome) DNAs,
2) PCR amplification of target genes,
3) Immobilization of DNA probes on wells of microtiter plates,
4) Hybridization of PCR products with DNA probes,
5) Detection of signals, and
6) Determination of the allele type.

1) Extraction of Chromosome(genome) DNAs

A method for preparation of genome DNAs is explained as follows. Leukocytes are isolated from collected blood according to usual methods and are lysed in a guanidine thiocyanate buffer. Proteins are eliminated by phenol extraction. A sodium acetate buffer (pH 5.2) is added and mixed. Genome DNAs are obtained by adding chilled ethanol.

2) PCR Amplification of Target Genes

The region containing the HLA class I allele is amplified by the PCR method using genome DNAs described above for a template. Commercialized reagents can be used for amplification described above. Amplification can be performed according to attached instructions. If it is necessary, reaction temperature, reaction time, the number of cycles and so on can be changed. Then, the amplification is performed by using a primer pair for a reaction tube. Amplification by adding multiple primer pairs into the same reaction tubes, can decrease operation task or cost. From the viewpoint of the purpose of this invention, a primer pair which one of them is biotinylated, is used for the practical testing or a kit.

For example, A2-5T and 5'-biotinylated A3-273T can be used for a primer pair to amplify the region containing the exon 2, the intron 2 and the exon 3 of the HLA-A2 alleles by the PCR method. A4-8C and 5'-biotinylated A4-254G can be used for a primer pair to amplify the region containing the exon 4 of the HLA-A alleles by the PCR method. These primers are described in the reference of the inventors (Tissue Antigens 1997 described above)

For example, BASF-1 and 5'-bitinylated BASR-1 can be used for a primer pair to amplify the region containing the exon 2, the intron 2 and the exon 3 of the HLA-B40 alleles by the PCR method.

For example, CGA011 or CGA012, and 5'-biotinylated AIn3-66C can be used for a primer pair to amplify the region containing the exon 2, the intron 2 and the exon 3 of all the HLA-A alleles by the PCR method.

For example, 5BIN1-TA (SEQ ID No.:93) or 5BIN1-CG (SEQ ID No.:94) and 5'-biotinylated 3BIN3-37 (SEQ ID No.:95) can be used for a primer pair to amplify the region containing the exon 2, the intron 2 and the exon 3 of all the HLA-B alleles by the PCR method. The primers are described in the reference of Cereb N. et al (Tissue Antigens 1997, Vol.50, 74-76)

For example, 5BCIn37-34C, 5BCIn37-24g or 5BCIn37-34g2, and 5'-biotinylated 3BCIn3-12 (SEQ ID No.:98) can be used for a primer pair to amplify the region containing the exon 2, the intron 2 and the exon 3 of all the HLA-C alleles by the PCR method. The primer, 3BCIn3-12, is described in the reference of Cereb N. et al (Tissue Antigens 1995, Vol.45, 1-11).

3) Immobilization of DNA Probes on Wells of Microtiter Plates

Amino-modified DNA probes (1–20 pmol) which can specifically hybridize with the sequence of at least one specific HLA-A allele, at least one specific HLA-B allele or at least one specific HLA-C allele, are added onto each well of carboxylate-modified polystyrene microtiter plates and immobilized covalently by inducing the chemical amino-binding reaction using a suitable catalyst, for example, 1-ethyl-3-(3-dimethylaminopropyl) carbodiimide (EDC). After immobilization of the DNA probes on wells, microtiter plates are washed with a suitable buffer. After washing, microtiter plates can be stored over an extended period of time on wet and cold condition.

4) Hybridization of PCR Products with DNA Probes

The PCR amplified products are denatured to a single strand DNA under strong alkali, for example, NaOH, and are hybridized with DNA probes which are immobilized on wells of microtiter plates. The hybridization is performed in a solution containing about 20% formamide on hybridization condition at about 37° C. After the hybridization, excessive amplified products or those which don't have the specific sequence to DNA probes described above, are eliminated. DNA probes used at this step are selected in compliance with the specific HLA class I gene or the specific group which are amplified at the above step.

For example, as for the amplified products from the region containing the exon 2, the intron 2 and the exon 3 of the HLA-A2 alleles by a primer pair described above, A2-5T and A3-273T, or the amplified products from the exon 4 of the HLA-A alleles by a primer pair, A4-8C and A4-254G, the hybridization can be performed by using A98T, A98A, A160A, A240T, A270T, A290T, A355G, A362TA, A362TT, A368A, A368G, A368T, A402G, A485A, A527A, A539A, A539T A559G, A570CG, A779A or A843A for DNA probes.

For example, as for the amplified products from the region containing the exon 2, the intron 2 and the exon 3 of the HLA-B40 alleles by a primer pair described above, BASF-1 and BASR-1, the hybridization can be performed by using BL4, BL5, BL24, BL25, BL34, BL35, BL37, BL39, BL41, BL50, BL56, BL57, BL222A, BL409T or BL512 for DNA probes.

For example, as for the amplified products from the region containing the exon 2, the intron 2 and the exon 3 of all the HLA-A alleles by a primer pair described above, CGA011, CGA012 or AIn3-66C, the hybridization can be performed by using A34, A239A, A238A, A257TC, A259AC, A282C, A282CT, A290TR, A299T, A355G, A414A, A448C, A468T, A489A, A502C, A526T, A538CG, A538TG, A539A, A539T, A555T, A570CG, A570GT or A302GR for DNA probes.

For example, as for the amplified products from the region containing the exon 2, the intron 2 and the exon 3 of all the HLA-B alleles by a primer pair described above, 5BIN1-TA, 5BIN1-CG or 3BIN3-37, the hybridization can be performed by using BL1, BL3, BL4, BL9, BL10, BL11, BL34, BL36, BL37, BL38, BL39R, BL40, BL41, BL42, BL77, BL78, BL79, BL226G, BL263T, BL272A, BL527A, BL538CG, BL538G or BL570GT for DNA probes.

For example, as for the amplified products from the region containing the exon 2, the intron 2 and the exon 3 of all the HLA-C alleles by a primer pair described above, 5BCIn37-34C, 5BCIn-37-24g, 5BCIn37-34g2 or 5BCIn3-12, the hybridization can be performed by using 201g1, C206gR, A-12, RA-2, A-3, RA-41, A-54, B-1, RB-28, C-12, C-24, C-33, C-43, 134-g, 134-A2, 353TCA1, 343A, R341A, R343g3, 353TCC, 361T1, 361T368g, 361T368T1, 369C, 387g1, 526AC2 or 538gAC for DNA probes.

About the concrete type of the HLA class I allele which are distinguished by the hybridization with these DNA probes, examples and Figures can be referred.

Besides these DNA probes, A302G, A423T, A524G, BL272GA, BL292G, BL292T, BL361G, CC, A-2, A-4 or B-2 can be used for typing of the HLA class I antigens or alleles described below. A302G, A423T and A524G can specifically hybridize with the sequence of the HLA-A antigens or alleles, A*2501 and A*3201, A*2501, A26, A34, A*4301 and A66, and A*2301, A29, A*31012, A*3201, A33 and A*7401, respectively. BL272GA, BL292G, BL292T and BL361G can specifically hybridize with the sequence of the HLA-B antigens or alleles, B14, B38 and B39, B7, B8, B14, B27, B39, B*4201, B*4601, B*5401, B55, B56, B67, B*7301, B*7801 and B*8101, B13, B15, B18, B35, B37, B38, B40, B41, B44, B*4501, B*4701, B48, B*4901, B*5001, B51, B52, B5301, B57, B58, B*5901 and B*7802, and B57, respectively. CC can hybridize with the sequence of all the HLA-C alleles. A-2, A-4 and B-2 can specifically hybridize with the sequence of the HLA-C antigens or alleles, Cw2, Cw3, Cw*0403 and Cw15, Cw*0602, Cw7 and Cw18, and Cw1, Cw3, Cw7, Cw8, Cw*1202, Cw*1203, Cw*1301, Cw14, Cw*1601 and Cw*16041, respectively.

5) Detection of Signals

An example for detection of signals is explained below. The PCR amplified products hybridizing with DNA probes can be detected by utilizing a label, which they have in themselves, such as a biotin. After an alkaline phosphate-conjugated streptavidin or a peroxidase-conjugated streptavidin which can bond to a biotin, is added to each well of the microtiter plates, and the plates are sealed, the reaction is performed by incubation on proper temperature condition. The hybridizing amplified products are detected as signals by using a chromogenic substrate such as p-nitrophenylphosphate (PNPP) or 3,3',5,5'-tetramethylbenzidine (TMB). Detection of signals is performed by measurement of the absorbance. The signals described above can be automatically detected by using a machine, and those by color development can be easily detected by the naked eye.

6) Determination of the Allele Types

Figure 3:
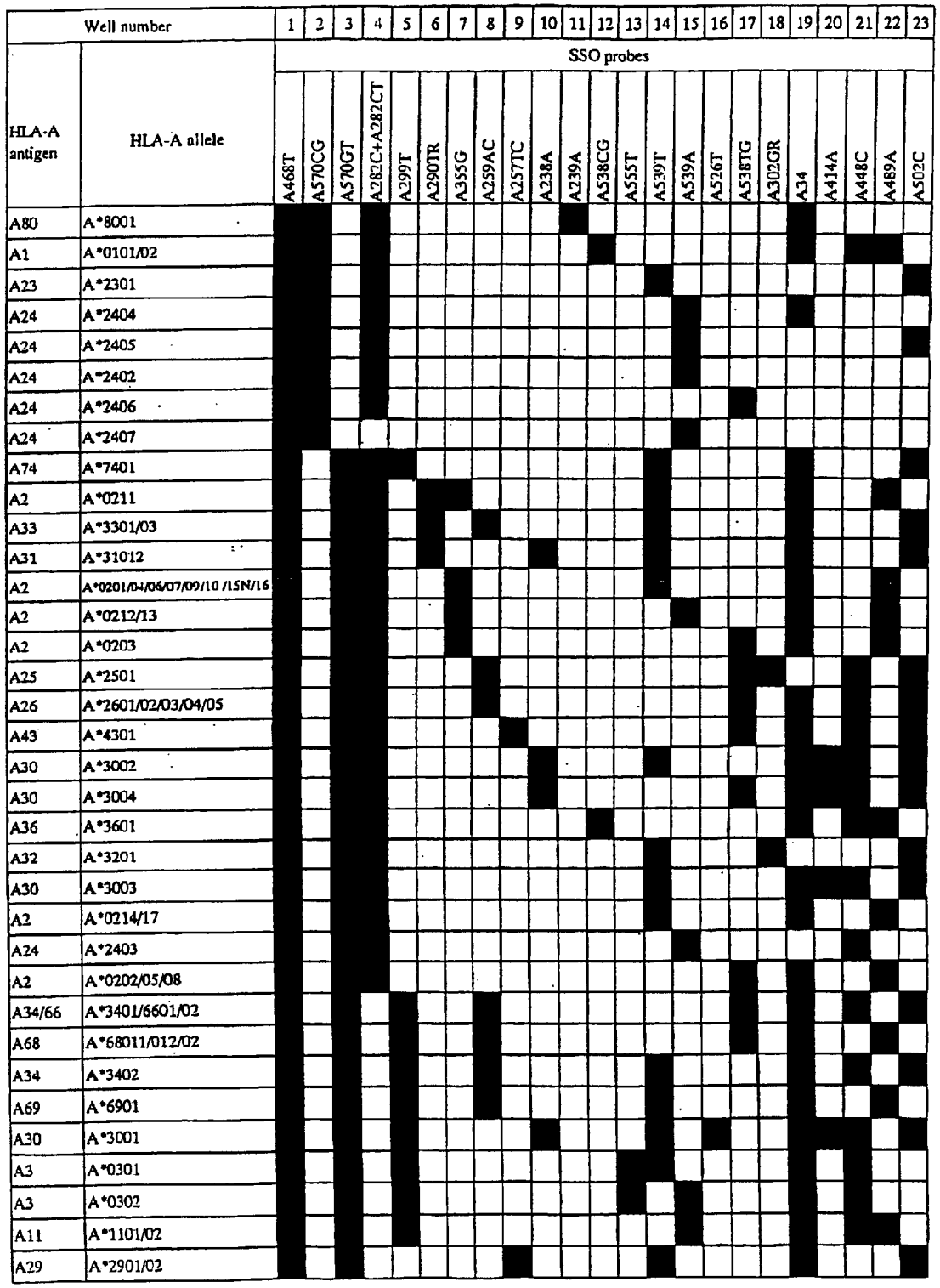
FIG. 3 indicates a Typing Table showing the reaction pattern between samples which the HLA-A antigen and allele type are known, and DNA probes in the present invention. Each name of DNA probes is shown on the top in the Figure, and each type of the HLA-A antigens and alleles is shown on the left side in the Figure. Closed square and Open square mean a positive and a negative reaction, respectively.
Figure 6:
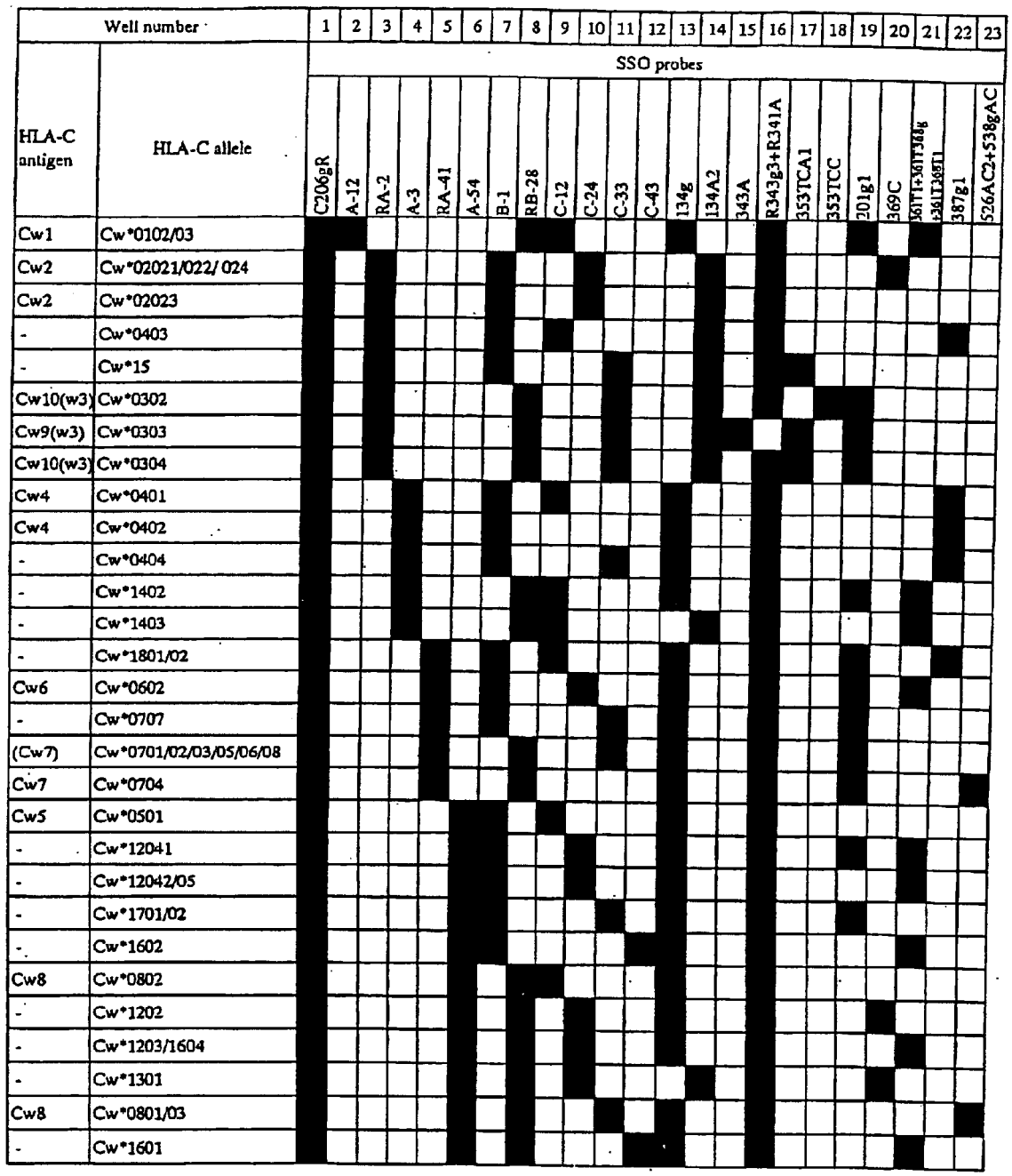
FIG. 6 indicates a Typing Table showing the reaction pattern between samples which the HLA-C antigen and/or allele type is known, and DNA probes in the present invention. Each name of DNA probes is shown on the top in Figure, and each type of the HLA-C and/or alleles is shown on the left side in Figure. Closed square and Open square mean a positive and a negative reaction, respectively.

By signal patterns which are detected on the microtiter plate described above, for example, in compliance with the Typing Tables which are disclosed in FIGS. 1–6, the HLA lass I alleles are determined. Patterns of these Typing Tables in FIGS. 1–6 can be arranged in case of necessity.

EXAMPLE

This invention is explained in more detail by showing examples, which are actually performed by using samples, whose HLA types are known. However, the range of this invention is not limited to only these examples.

Example 1

HLA-A2 Allele Typing

Leukocytes (Samples 1–4) which were isolated from peripheral blood (about 10 ml) of normal subjects according to usual methods, were lysed in 500 µl of guanidine thiocyanate buffer (4M guanidine thiocyanate, 25 mM sodium citrate(pH7.0), 0.5% sodium N-lauroylsarcosinate, 1% mercaptoethanol). The solution was extracted twice with phenol to eliminate proteins. After mixing with 3M sodium acetate buffer (pH 5.2), genome DNAs were obtained by adding twice volume of chilled ethanol. By using this DNAs, typing of the HLA-A2 alleles was performed as follows.

By using A2-5T and 5'-biotinylated A3-273T for a primer pair, amplification of the region containing the exon 2, the intron 2 and the exon 3 of the HLA-A2 alleles from DNAs described above was performed by the PCR method. Likewise, by using A4-8C and 5'-biotinylated A4-254G for a primer pair, amplification of the region containing the exon 4 of the HLA-A alleles was also performed by the PCR method. The reaction solution was composed of genomic DNAs (100 ng), 1.4 units of thermostable DNA polymerase which was pretreated with Taq Start™ Antibody for 5 min at room temperature, 67 mM Tris-HCl (pH 8.8), 16.6 mM ammonium sulfate, 1.5 mM magnesium chloride, 0.01% Tween 20, 200 µM dNTPs, and each 1.7 µM of a primer pair in a final volume of 80 µl. DNA amplification was performed by using GeneAmp PCR system 9600 (Perkin Elmer) by initial denaturation at 95° C. for 2 min followed by 5 cycles of denaturation for 25 s, annealing at 70° C. for 45 s, extension at 72° C. for 45 s followed by 36 cycles of denaturation for 25 s, annealing at 65° C. for 50 s, extension at 72° C. for 45 s.

5'-amino-modified DNA probes, A98T, A98A, A160A, A240T, A270T, A290T, A355G, A362TA, A362TT, A368A, A368G, A368T, A402G, A485A, A527A, A539A, A539T A559G, A570CG, A779A and A843A, were immobilized covalently on wells of carboxylate-modified polystyrene microtiter plates as follows. Twenty-five µl of the DNA probes described above which were dissolved with sterile distilled water, was added to each of 20 wells which were used for a sample, in order shown in FIG. 1. Next, 75 µl of 0.2M 1-ethyl-3-(3-dimethylaminopropyl)carbodiimide (EDC) was added to each well and mixed. After the plates were sealed and incubated for 16 hours at room temperature, they were washed four times with PBS buffer (7.5 mM di-potassium hydrogenphosphate, 2.5 mM potassium dihydrogenphosphate, 0.15M sodium chloride). Two hundreds µl of 0.4N NaOH were added to each well and the plates were incubated for 1 hour at 37° C. The plates were washed four times with PBS buffer.

One hundred µl of GMC buffer for hybridization (0.25M di-sodium hydrogenphosphate, 7% SDS, 1% BSA, 0.5M EDTA, 0.03M phosphoric acid, 20% formamide) was added to each well of the microtiter plates and the plates were incubated for 5 min at 37° C. After incubation, the buffer was removed from each well. During incubation, 72 µl of the amplified products which were obtained from the region containing the exon 2, the intron 2 and the exon 3, and 8 µl of the amplified products which were obtained from the region containing the exon 4, were denatured with an equivalent volume of 0.4 NaOH for 5 min at room temperature. After denaturation, 1800 µl and 200 µl of hybridization buffer were added to the denatured products, respectively, mixed and 100 µl of them was added to each well (the former was added Well 1 to Well 18. The latter was added to Well 19 and Well 20). The microtiter plates were sealed and incubated for 1 hour at 37° C.

The microtiter plates were sealed and incubated for 45 min at 37° C. After the solution was removed from wells, the plates were washed five times with 2×SSC washing solution (0.3M sodiumchloride, 0.03M tri-sodiumcitrate), 100 µl of alkaline phosphatase-conjugated streptavidin (Gibco BRL) solution, diluted to 1/1000 in TTBS enzyme diluting solution (0.2M Tris-HCl (pH7.6), 0.5M sodium chloride, 0.5% Tween 20), was added to each well. After the solution was removed from wells, the plates were washed five times with the washing solution described above, chromogenic substrate solution (4 mg/ml PNPP (p-nitrophenylphosphate), 1 mM magnesium chloride, 10% diethanolamine (pH9.8)) was added and incubated for 30 min at 37° C. After incubation, color development was stopped by adding 25 µl of 0.5M EDTA to each well and the absorbance was measured at 405 mm. The absorbance to each sequence is shown in Table 1. The absorbance of positive and negative signals was 1.0 and over, and under 0.5, respectively. By using these results, BLA-A2 allele typing for each sample (1–4) was performed according to the Typing Table shown in FIG. 1. The typing results are shown in the bottom column of Table 1 as follows.

TABLE 1

Results of HLA-A2 allele typing (the absorbance at 405nm)

| Well | SSO probe | Sample 1 | Sample 2 | Sample 3 | Sample 4 |
| --- | --- | --- | --- | --- | --- |
| 1 | A240T | 1.894 | 1.907 | 2.049 | 1.849 |
| 2 | A368A | 1.675 | 1.744 | 0.116 | 1.210 |
| 3 | A368G | 0.265 | 0.294 | 2.050 | 0.198 |
| 4 | A368T | 0.077 | 0.212 | 0.038 | 0.065 |
| 5 | A362TT + A362TA | 0.282 | 0.261 | 0.052 | 0.202 |
| 6 | A98T | 1.655 | 0.084 | 1.768 | 1.406 |
| 7 | A98A | 0.047 | 1.871 | 0.038 | 1.589 |

TABLE 1-continued

Results of HLA-A2 allele typing (the absorbance at 405nm)

| Well | SSO probe | Sample 1 | Sample 2 | Sample 3 | Sample 4 |
| --- | --- | --- | --- | --- | --- |
| 8 | A539T | 1.952 | 1.971 | 1.974 | 1.127 |
| 9 | A539A | 0.267 | 0.280 | 0.380 | 0.232 |
| 10 | A402G | 0.299 | 0.344 | 0.326 | 0.227 |
| 11 | A527A | 0.499 | 0.212 | 0.229 | 0.140 |
| 12 | A270T | 0.194 | 0.265 | 0.263 | 0.229 |
| 13 | A290T | 0.118 | 0.104 | 0.105 | 0.112 |
| 14 | A559G | 0.027 | 0.019 | 0.026 | 0.048 |
| 15 | A485A | 0.171 | 0.176 | 0.169 | 0.108 |
| 16 | A355G | 1.956 | 1.971 | 1.877 | 1.344 |
| 17 | A160A | 0.024 | 0.024 | 0.030 | 0.030 |
| 18 | A570CG | 0.040 | 0.027 | 0.050 | 0.064 |
| 19 | A779A | 0.020 | 0.021 | 0.034 | 0.041 |
| 20 | A843A | 0.025 | 0.049 | 0.038 | 0.045 |
| HLA-A2 Allele type | | A*0201 | A*0206 | A*0207 | A*0201/ 0206 |

Example 2

HLA-B40 Allele Typing

Leukocytes (Samples 5–8) which were isolated from peripheral blood (about 10 ml) of normal subjects according to usual methods, were lysed in 500 µl of guanidine thiocyanate buffer (4M guanidine thiocyanate, 25 mM sodium citrate(pH7.0), 0.5% sodium N-lauroylsarcosinate, 1% mercaptoethanol). The solution was extracted twice with phenol to eliminate proteins. After mixing with 3M sodium acetate buffer (pH 5.2, genome DNAs were obtained by adding twice volume of chilled ethanol. By using this DNAs, typing of the HLA-B40 alleles was performed as follows.

By using BASF-1 and 5'-biotinylated BASR-1 for a primer pair, amplification of the region containing the exon 2, the intron 2 and the exon 3 of the HLA-B40 alleles from DNAs described above was performed by the PCR method. The reaction solution was composed of genomic DNAs (100 ng), 1.4 units of thermostable DNA which was pretreated with Taq Start™Antibody for 5 min at room temperature, 33.5 mM Tris-HCl (pH 8.8), 8.8 mM ammonium sulfate, 1.5 mM magnesium chloride, 0.005% Tween 20, 200 µM dNTPs, and each 1.7 µM of a primer pair in a final volume of 70 µl. DNA amplification was performed by using Gene-Amp PCR system 9600 (Perkin Elmer) by initial denaturation at 95° C. for 2 min followed by 5 cycles of denaturation for 25 s, annealing at 70° C. for 45 s, extension at 72° C. for 45 s followed by 36 cycles of denaturation for 25 s, annealing at 65° C. for 50 s, extension at 72° C. for 45 s.

5'-amino-modified DNA probes, BL4, BL5, BL24, BL25, BL34, BL35, BL37, BL39, BL41, BL50, BL56, BL57, BL222A, BL409T and BL512T, were immobilized covalently on wells of carboxylate-modified polystyrene microtiter plates as follows. Twenty-five µl of the DNA probes described above which were dissolved with sterile distilled water, was added to each of 15 wells which were used for a sample, in order shown in FIG. 2. Next, 75 µl of 0.2M EDC was added to each well and mixed. After the plates were sealed and incubated for 16 hours at room temperature, they were washed four times with PBS buffer solution (7.5 mM di-potassium hydrogenphosphate, 2.5 mM potassium dihydrogenphosphate, 0.15M sodium chloride). Two hundreds µl of 0.44N NaOH were added to each well and the plates were incubated for 1 hour at 37° C. The plates were washed four times with PBS buffer solution.

One hundred μl of GMC buffer (0.25M di-sodium hydrogenphosphate, 7% SDS, 1% BSA, 0.5M EDTA, 0.03M phosphoric acid, 20% formamide) was added to each well of the microtiter plates and the plates were incubated for 5 min at 37° C. After incubation, the buffer was removed from each well. During incubation, 60 μl of the amplified products described above, were denatured with an equivalent volume of 0.4 NaOH for 5 min at room temperature. After denaturation, 1500 μl of hybridization buffer was added to the denatured product, mixed and 100 μl of them was added to each well. The microtiter plates were sealed and incubated for 1 hour at 37° C.

After the solution was removed from wells, the plates were washed five times with 2×SSC washing solution (0.3M sodium chloride, 0.03M tri-sodium citrate), 100 μl of peroxidase-conjugated streptavidin (Vector Laboratories) solution, diluted to 1/2000 in TTBS enzyme diluting solution (0.2M Tris-HCl (pH7.6), 0.5M sodium chloride, 0.5% Tween 20), was added to each well. The microtiter plates were sealed and incubated for 15 min at 37° C. After the solution was removed from wells, the plates were washed five times with the washing solution described above, chromogenic substrate solution (3,3',5,5'-tetramethylbenzidine (TMB) solution:Kirkegaard & Perry Laboratories) was added and incubated for 30 min at 37° C. After incubation, color development was stopped by adding 100 μl of 1% SDS to each well and the absorbance was measured at 650 mm. The absorbance to each sequence is shown in Table 2. The absorbance for positive and negative signals was 1.0 and over, and under 0.5, respectively. By using these results, HLA-B40 allele typing for each sample (5–8) was performed according to the Typing Table shown in FIG. 2. The typing results are shown in the bottom column of Table 2 as follows.

TABLE 2

Results of HLA-B40 allele typing (the absorbance at 650nm)

| Well | SS0 probe | Sample 5 | Sample 6 | Sample 7 | Sample 8 |
|---|---|---|---|---|---|
| 1 | BL222A | 1.846 | 1.671 | 1.742 | 1.849 |
| 2 | BL34 | 2.126 | 2.148 | 2.182 | 2.239 |
| 3 | BL35 | 0.088 | 0.082 | 0.083 | 0.093 |
| 4 | BL4 | 1.966 | 1.870 | 1.800 | 1.976 |
| 5 | BL5 | 0.154 | 0.161 | 0.142 | 0.205 |
| 6 | BL24 | 1.711 | 1.744 | 1.671 | 2.018 |
| 7 | BL25 | 0.050 | 0.051 | 0.056 | 0.067 |
| 8 | BL512T | 2.356 | 0.209 | 0.238 | 0.058 |
| 9 | BL37 | 0.130 | 2.533 | 2.517 | 0.014 |
| 10 | BL39 | 0.069 | 0.099 | 0.111 | 0.027 |
| 11 | BL41 | 0.042 | 0.064 | 0.070 | 2.315 |
| 12 | BL50 | 0.101 | 0.014 | 0.039 | 0.044 |
| 13 | BL56 | 2.487 | 2.464 | 0.373 | 2.342 |
| 14 | BL57 | 0.193 | 0.156 | 2.124 | 0.093 |
| 15 | BL409T | 0.038 | 0.050 | 0.287 | 0.031 |
| HLA-B40 Allele type | | B*4001 | B*4002 | B*4003 | B*4006 |

Example 3

HLA-A Antigen and Allele Typing

Leukocytes (Samples 9–12) which were isolated from peripheral blood (about 10 ml) of normal subjects according to usual methods, were lysed in 500 μl of guanidine thiocyanate buffer(4M guanidine thiocyanate, 25 mM sodium citrate(pH7.0), 0.5% sodium N-lauroylsarcosinate, 1% mercaptoethanol). The solution was extracted twice with phenol to eliminate proteins. After mixing with 3 M sodium acetate buffer (pH5.2), genome DNAs were obtained by adding twice volume of chilled ethanol. By using this DNAs, typing of the HLA-A antigens and alleles was performed as follows.

By using CGA011, CGA012 and 5'-biotinylated AIn3-66C for a primer pair, amplification of the region containing the exon 2, the intron 2 and the exon 3 of the HLA-A alleles from DNAs described above was performed by the PCR method. The reaction solution was composed of genomic DNAs (100 ng), 1.4 units of thermostable DNA polymerase which was pretreated with Taq Start™ Antibody for 5 min at room temperature, 33.5 mM Tris-HCl (pH 8.8), 8.8 mM ammonium sulfate, 1.5 mM magnesium chloride, 0.005% Tween 20, 200 μM dNTPs, and each 1.7 μM of a primer pair (the ratio of CGA011 to CGA012 is 4 to 1) in a final volume of 100 μl. DNA amplification was performed by using GeneAmp PCR system 9600 (Perkin Elmer) by initial denaturation at 95° C. for 2 min followed by 5 cycles of denaturation for 25 s, annealing at 70° C. for 45 s, extension at 72° C. for 45 s followed by 36 cycles of denaturation for 25 s, annealing at 65° C. for 50 s, extension at 72° C. for 45 s.

5'-amino-modified DNA probes, A34, A239A, A238A, A257TC, A259AC, A282C, A282CT, A290TR, A299T, A302GR, A355G, A414A, A448C, A468T, A489A, A502C, A526T, A538CG, A538TG, A539A, A539T, A555T, A570CG and A570GT, were immobilized covalently on wells of carboxylate-modified polystyrene microtiter plates as follows. Twenty-five μl of the DNA probes described above which were dissolved with sterile distilled water, was added to each of 23 wells which were used for a sample, in order shown in FIG. 3. Next, 75 μl of 0.2M EDC solution was added to each well and mixed. After the plates were sealed and incubated for 16 hours at room temperature, they were washed four times with PBS buffer solution (7.5 mM di-potassium hydrogenphosphate, 2.5 mM potassium dihydrogenphosphate, 0.15M sodium chloride). Two hundreds μl of 0.4N NaOH were added to each well and the plates were incubated for 1 hour at 37° C. The plates were washed four times with PBS buffer solution.

One hundred μl of GMC buffer (0.25M di-sodium hydrogenphosphate, 7% SDS, 1% BSA, 0.5M EDTA, 0.03M phosphoric acid, 20% formamide) was added to each well of the microtiter plates and the plates were incubated at 37° C. for 5 min. After incubation, the buffer of each well was removed from each well. During incubation, 96 μl of the amplified products described above, were denatured with an equivalent volume of 0.4 NaOH for 5 min at room temperature. After denaturation, 2400 μl of hybridization buffer was added to the denatured products, mixed and 100 μg of them was added to each well. The microtiter plates were sealed and incubated for 1 hour at 37° C.

After the solution was removed from wells, the plates were washed five times with 2×SSC washing solution (0.3M sodium chloride, 0.03M tri-sodium citrate), 100 μl of peroxidase-conjugated streptavidin (Boehringer Mannheim) solution, diluted to 1/2000 in TTBS enzyme diluting solution (0.2M Tris-HCl (pH7.6), 0.5M sodium chloride, 0.5% Tween 20), was added to each well. The microtiter plates were sealed and incubated for 15 min at 37° C. After the solution was removed from wells, the plates were washed five times with the washing solution described above, chromogenic substrate solution (THB solution:Kirkegaard & Perry Laboratories) was added and incubated for 30 min at 37° C. After incubation, color development was stopped by adding 100 μl of 1% SDS to each well and the absorbance was measured at 650 mm. The absorbance for positive and negative signals was 1.0 and over, and under 0.5, respectively. By using these results, HLA-A antigen and allele typing for each sample (9–12) was performed according to the Typing Table shown in FIG. 3. The typing results are shown in the bottom column of Table 3 as follows.

TABLE 3

Results of HLA-A antigen and allele typing (the absorbance at 650nm)

| Well | SSO probe | Sample 9 | Sample 10 | Sample 11 | Sample 12 |
|---|---|---|---|---|---|
| 1 | A468T | 2.963 | 3.046 | 2.603 | 2.719 |
| 2 | A570CG | 0.087 | 2.951 | 0.081 | 2.847 |
| 3 | A570GT | 2.815 | 0.065 | 2.690 | 2.763 |
| 4 | A282C + A282CT | 1.950 | 2.825 | 2.538 | 2.552 |
| 5 | A299T | 0.111 | 0.119 | 0.279 | 0.162 |
| 6 | A290TR | 0.012 | 0.135 | 2.245 | 0.095 |
| 7 | A355G | 2.382 | 0.033 | 0.037 | 0.128 |
| 8 | A259AC | 0.048 | 0.063 | 0.095 | 2.127 |
| 9 | A257TC | 0.034 | 0.021 | 0.054 | 0.060 |
| 10 | A238A | −0.016 | 0.011 | 1.907 | 0.041 |
| 11 | A239A | 0.037 | 0.052 | 0.061 | 0.187 |
| 12 | A538CG | 0.012 | 0.025 | 0.017 | 0.065 |
| 13 | A555T | 0.068 | 0.038 | 0.066 | 0.090 |
| 14 | A539T | 2.480 | 0.048 | 1.618 | 0.093 |
| 15 | A539A | 0.111 | 2.513 | 0.205 | 2.402 |
| 16 | A526T | 0.023 | 0.046 | 0.105 | 0.065 |
| 17 | A538TG | 0.109 | 0.118 | 0.092 | 2.125 |
| 18 | A302GR | −0.020 | 0.169 | 0.030 | 0.237 |
| 19 | A34 | 2.186 | 0.121 | 1.441 | 2.271 |
| 20 | A414A | 0.031 | 0.127 | 0.079 | 0.095 |
| 21 | A448C | 0.232 | 0.091 | 0.073 | 2.412 |
| 22 | A489A | 2.896 | 0.100 | 0.051 | 0.276 |
| 23 | A502C | 0.017 | 0.135 | 1.401 | 2.517 |
| HLA-A antigen and Allele type | | A2/- | A24/- | A*31012/- | A24/26 |

Example 4

HLA-B Antigen and Allele Typing

Leukocytes (Samples 13–16) which were isolated from peripheral blood (about 10 ml) of normal subjects according to usual methods, were lysed in 500 μl of guanidine thiocyanate buffer (4M guanidine thiocyanate, 25 mM sodium citrate(pH7.0), 0.5% sodium N-lauroylsarcosinate, 1% mercaptoethanol). The solution was extracted twice with phenol to eliminate proteins. After mixing with 3 M sodium acetate buffer (pH5.2), genome DNAs were obtained by adding twice volume of chilled ethanol. By using the DNAs, typing of the HLA-B antigen and allele was performed as follows.

By using 5BIN1-TA, 5BIN1-CG and 5'-biotinylated 3BIN3-37 for a primer pair, amplification of the region containing the exon 2, the intron 2 and the exon 3 of the HLA-B alleles from DNAs described above was performed by the PCR method. The reaction solution was composed of genomic DNAs (100 ng), 1.4 units of thermostable DNA polymerase which was pretreated with Taq Start™ Antibody for 5 min at room temperature, 67 mM Tris-HCl (pH 8.8), 16.6 mM ammonium sulfate, 1.5 mM magnesium chloride, 0.01% Tween 20, 10% DMSO, 200 μM dNTPs, and each 1.7 μM of a primer pair (the ratio of 5BIN1-TA to 5BIN-CG is 2 to 3) in a final volume of 100 μl. DNA amplification was performed by using GeneAmp PCR system 9600 (Perkin Elmer) by initial denaturation at 95° C. for 2 min followed by 5 cycles of denaturation for 25 s, annealing at 70° C. for 45 s, extension at 72° C. for 45 s followed by 36 cycles of denaturation for 25 s, annealing at 65° C. for 50 s, extension at 72° C. for 45 s.

5'-amino-modified DNA probes, BL1, BL3, BL4, BL9, BL10, BL11, BL34, BL36, BL37, BL38, BL39R, BL40, BL41, BL42, BL77, BL78, BL79, BL226G, BL263T, BL272A, BL527A, BL538CG, BL538G and BL570GT, were immobilized covalently on wells of carboxylate-modified polystyrene microtiter plates as follows. Twenty-five μl of the DNA probes described above which were dissolved with sterile distilled water, was added to each of 23 wells which were used for a sample, in order shown in FIGS. 4 and 5. Next, 75 μl of 0.2M EDC was added to each well and mixed. After the plates were sealed and incubated for 16 hours, they were washed four times with PBS buffer solution (7.5 mM di-potassium hydrogenphosphate, 2.5 mM potassium dihydrogenphosphate, 0.15M sodium chloride). Two hundred μl of 0.4N NaOH were added to each well and the plates were incubated for 1 hour at 37° C. The plates were washed four times with PBS buffer solution.

One hundred μl of GMC buffer (0.25M di-sodium hydrogenphosphate, 7% SDS, 1% BSA, 0.5M EDTA, 0.03M phosphoric acid, 20% formamide) was added to each well of the microtiter plates and the plates were incubated for 5 min at 37° C. After incubation, the buffer was removed from each well. During incubation, 96 μl of the amplified products described above, were denatured with an equivalent volume of 0.4 NaOH for 5 min at room temperature. After denaturation, 2400 μl of hybridization buffer was added to the denatured products, mixed and 100 μl of them was added to each well. The microtiter plates were sealed and incubated for 1 hour at 37° C.

After the solution was removed from wells, the plates were washed five times with 2×SSC washing solution (0.3M sodium chloride, 0.03M tri-sodium citrate), 100 μl of peroxidase-conjugated streptavidin (Boehringer Mannheim) solution, diluted to ½₀₀₀ in TTBS enzyme diluting solution (0.2M Tris-HCl(pH7.6), 0.5M sodium chloride, 0.5% Tween 20), was added to each well. The microtiter plates were sealed and incubated for 15 min at 37° C. After the solution was removed from wells, the plates were washed five times with the washing solution described above, chromogenic substrate solution (TMB solution:Kirkegaard & Perry Laboratories) was added and incubated for 30 min at 37° C. After incubation, color development was stopped by adding 100 μl of 1% SDS to each well and the absorbance was measured at 650 mm. The absorbance for positive and negative signals was 1.0 and over, and under 0.5, respectively. By using these results, HLA-B antigen and allele typing for each sample (13–16) was performed according to the Typing Tables shown in FIGS. 4 and 5. The typing results are shown in the bottom column of Table 4 as follows.

TABLE 4

Results of HLA-B antigen and allele typing (the absorbance at 650nm)

| Well | SSO probe | Sample 13 | Sample 14 | Sample 15 | Sample 16 |
|---|---|---|---|---|---|
| 1 | BL36 | 0.064 | 0.131 | 0.101 | 0.087 |
| 2 | BL37 | 2.155 | 0.055 | 0.021 | 0.009 |
| 3 | BL38 | 0.447 | 0.150 | 0.110 | 0.071 |
| 4 | BL39R | 0.147 | 1.476 | 0.143 | 0.103 |
| 5 | BL40 | 0.026 | 0.040 | 0.290 | 0.211 |
| 6 | BL41 | 0.064 | 0.062 | 2.650 | 2.213 |
| 7 | BL42 | 0.268 | 0.235 | 0.237 | 0.120 |
| 8 | BL77 | 2.564 | 0.038 | 0.075 | 0.128 |
| 9 | BL78 | 0.104 | 2.559 | 2.549 | 2.627 |
| 10 | BL79 | 0.115 | 0.232 | 0.199 | 2.316 |
| 11 | BL1 | 0.080 | 1.065 | 0.176 | 0.241 |
| 12 | BL9 | 1.787 | 0.124 | 0.058 | 1.142 |
| 13 | BL3 | 0.173 | 0.163 | 0.141 | 0.144 |

TABLE 4-continued

Results of HLA-B antigen and allele typing (the absorbance at 650nm)

| Well | SSO probe | Sample 13 | Sample 14 | Sample 15 | Sample 16 |
|---|---|---|---|---|---|
| 14 | BL4 | 0.055 | 1.720 | 0.142 | 0.215 |
| 15 | BL10 | 2.256 | 0.051 | 0.066 | 1.847 |
| 16 | BL11 | 0.178 | 0.064 | 0.264 | 0.054 |
| 17 | BL272A | 0.038 | 0.105 | 0.044 | 0.071 |
| 18 | BL226G | 0.034 | 0.163 | 0.137 | 0.102 |
| 19 | BL263TA | 0.005 | 0.173 | 0.048 | 0.012 |
| 20 | BL34 | 1.992 | 0.168 | 0.186 | 2.446 |
| 21 | BL527A | 2.674 | 0.383 | 2.369 | 1.948 |
| 22 | BL538CG + BL538G | 2.619 | 0.311 | 0.354 | 0.356 |
| 23 | BL570GT | 2.538 | 0.421 | 2.645 | 2.821 |
| HLA-B antigen and allele type | | B7/- | B*4403/- | B51/- | B51/55 |

Example 5

HLA-C Allele Typing

Leukocytes (Samples 17–20) which were isolated from peripheral blood (about 10 ml) of normal subjects according to usual methods, were lysed in 500 μl of guanidine thiocyanate buffer (4M guanidine thiocyanate, 25 mM sodium citrate(pH7.0), 0.5% sodium N-lauroylsarcosinate, 1% mercaptoethanol). The solution was extracted twice with phenol to eliminate proteins. After mixing with 3M sodium acetate buffer (pH5.2), genome DNAs were obtained by adding twice volume of chilled ethanol. By using the DNAs, typing of the HLA-C alleles was performed as follows.

By using 5BCIn37-24C, 5BCIn-37-24g and 5'-biotinylated 5BCIn37-34g2 for a primer pair, amplification of the region containing the exon 2, the intron 2 and the exon 3 of the HLA-C alleles from DNAs described above was performed by the PCR method. The reaction solution was composed of genomic DNAs (100 ng), 1.4 units of thermostable DNA polymerase which was pretreated with Taq Start™Antibody for 5 min at room temperature, 33.5 mM Tris-HCl (pH 8.8), 8.8 mM ammonium sulfate, 1.5 mM magnesium chloride, 0.005% Tween 20, 200 μM dNTPs, and each 1.7 μM of a primer pair in a final volume of 100 μl. DNA amplification was performed by using GeneAmp PCR system 9600 (Perkin Elmer) by initial denaturation at 95° C. for 2 min followed by 5 cycles of denaturation for 25 s, annealing at 70° C. for 45 s, extension at 72° C. for 45 s followed by 36 cycles of denaturation for 25 s, annealing at 65° C. for 50 s, extension at 72° C. for 45 s.

5'-amino-modified DNA probes, 201g1, C206gR, A-12, RA-2, A-3, RA-41, A-54, B-1, RB-28, C-12, C-24, C-33, C-43, 134-g, 134-A2, 353TCA1, R341A, 343A. R343g3, 353TCC, 361T1, 361T368g, 361T368T1, 369C, 387g1, 526AC2 and 538gAC, were immobilized covalently on wells of carboxylate-modified polystyrene microtiter plates as follows. Twenty-five μl of the DNA probes described above which were dissolved with sterile distilled water, was added to each of 23 wells which were used for a sample, in order shown in FIG. 6. Next, 75 μl of 0.2M EDC solution was added to each well, mixed and sealed. After the plates were sealed and incubated for 16 hours, they were washed four times with PBS buffer solution (7.5 mM di-potassium hydrogenphosphate, 2.5 mM potassium dihydrogenphosphate, 0.15M sodium chloride). Two hundreds μl of 0.4N NaOH were added to each well and the plates were incubated for 1 hour at 37° C. The plates were washed four times with PBS buffer solution.

One hundred μl of GMC buffer (0.25M di-sodium hydrogenphosphate, 7% SDS, 1% BSA, 0.5M EDTA, 0.03M phosphoric acid, 20% formamide) was added to each well of the microtiter plates and the plates were incubated for 5 min at 37° C. After incubation, the buffer was removed from each well. During incubation, 96 μl of the amplified products described above, were denatured with an equivalent volume of 0.4 NaOH for 5 min at room temperature. After denaturation, 2400 μl of hybridization buffer solution was added to the denatured products, mixed and 100 μl of them was added to each well. The microtiter plates were sealed and incubated for 1 hour at 37° C.

After the solution was removed from wells, the plates were washed five times with 2×SSC washing solution(0.3M sodium chloride, 0.03M tri-sodium citrate). One hundredth of peroxidase-conjugated streptavidin (Boehringer Mannheim) solution, diluted to ½000 in TTBS enzyme diluting solution(O.2M Tris-HCl(pH7.6), 0.5M sodium chloride, 0.5% Tween 20), was added to each well. The microtiter plates were sealed and incubated for 15 min at 37° C. After the solution was removed from wells, the plates were washed five times with the washing solution described above, chromogenic substrate solution (TMB solution:Kirkegaard & Perry Laboratories) was added and incubated for 30 min at 37° C. After incubation, color development was stopped by adding 100 μl of 1% SDS to each well and the absorbance was measured at 650 mm. The absorbance for positive and negative signals was 1.0 and over, and under 0.5, respectively. By using these results, HLA-C allele typing for each sample (17–20) was performed according to the Typing Table shown in FIG. 6. The typing results are shown in the bottom column of Table 5 as follows.

TABLE 5

Results of HLA-C allele typing (the absorbance at 650nm)

| Well | SSO probe | Sample 17 | Sample 18 | Sample 19 | Sample 20 |
|---|---|---|---|---|---|
| 1 | C206gR | 2.080 | 2.069 | 2.003 | 1.871 |
| 2 | A-12 | 2.165 | -0.024 | -0.029 | 1.805 |
| 3 | RA-2 | 0.020 | 1.992 | 0.120 | 1.979 |
| 4 | A-3 | 0.069 | 0.038 | 0.052 | 0.081 |
| 5 | RA-41 | 0.008 | 0.033 | 0.121 | 0.102 |
| 6 | A-54 | -0.012 | 0.194 | 2.080 | 0.059 |
| 7 | B-1 | 0.202 | 0.124 | 0.145 | 0.233 |
| 8 | RB-28 | 2.403 | 1.640 | 1.716 | 1.998 |
| 9 | C-12 | 1.855 | 0.045 | 0.019 | 1.739 |
| 10 | C-24 | 0.138 | 0.064 | 2.002 | 0.287 |
| 11 | C-33 | 0.086 | 2.563 | 0.077 | 2.181 |
| 22 | C-43 | 0.113 | 0.182 | 0.137 | 0.174 |
| 13 | 134-g | 1.594 | 0.089 | 1.763 | 1.384 |
| 14 | 134-A2 | 0.049 | 2.096 | 0.291 | 1.380 |
| 15 | 343A | 0.021 | 2.672 | 0.047 | 1.480 |
| 16 | R343g3 + R341A | 2.562 | 0.292 | 2.717 | 1.928 |
| 17 | 353TCA1 | 0.001 | 2.551 | 0.157 | 1.740 |
| 18 | 353TCC | 0.021 | -0.002 | 0.092 | 0.006 |
| 19 | 201g1 | 1.209 | 1.679 | 0.176 | 1.225 |
| 20 | 369C | 0.055 | 0.183 | 2.640 | 0.163 |
| 21 | 361T1 + 361T368g + 361T368T1 | 2.345 | 0.040 | 0.048 | 1.885 |
| 22 | 387g1 | 0.028 | 0.054 | 0.015 | 0.019 |
| 23 | 526AC2 + 538gAC | 0.090 | 0.074 | 0.124 | 0.092 |

TABLE 5-continued

Results of HLA-C allele typing (the absorbance at 650nm)

| Well | SSO probe | Sample 17 | Sample 18 | Sample 19 | Sample 20 |
|---|---|---|---|---|---|
| HLA-C allele type | | C*0102/- | C*0303/- | C*1202/- | C*0102/ 0303 |

Industrial Applicability

By this invention, a single HLA class I antigen or allele is determined by combining PCR amplification using a primer pair which can amplify all the HLA-A alleles, all the HLA-B alleles or all the HLA-C alleles or which is specific to the common sequence to alleles of the specific group consisting of the specific HLA-A alleles or the specific HLA-B alleles, with reverse hybridization analysis using DNA probes to enable to specifically hybridize with the sequence of al least a specific HLA-A allele, at least a specific HLA-B allele or at least a specific HLA-C allele, which are covalently immobilized on wells of microtiter plates. Therefore, it can solve problems from the viewpoint of manipulation of HLA class I loci antigen typing by the classical serological method, and can classify at the allele level (allele typing) the class I antigens or subtypes to be unable to distinguish and classify by the classical method. Furthermore, at the same time, it can solve problems from the viewpoint of manipulation and resolution of HLA class I allele typing. Namely, this invention enables us to easily mechanize and automate detection and determination of the HLA class I alleles. This invention offers a method, a reagent and a kit for typing of the HLA class I alleles, which are useful for judgement of compatibility between a donor and a recipient in organ transplantation and for association analysis between the HLA class I genes and various kinds of diseases in the clinical and medical field.

What is claimed is:

1. A method for typing HLA class I alleles comprising the steps of:
   (a) providing nucleotide sequence(s) encoding HLA class I alleles or a fragment thereof as a template for PCR;
   (b) non-selectively amplifying all HLA-A alleles, all HLA-B alleles, or all HLA-C alleles by PCR using a primer pair which can amplify all the HLA-A alleles, all the HLA-B alleles, or all the HLA-C alleles, or selectively amplifying a specific group of HLA-A alleles or a specific group of HLA-B alleles by PCR using a primer pair which is specific to a common nucleotide sequence of the specific group;
   (c) adding the resulting PCR products to wells of microtiter plates, wherein each well is modified with a carboxyl group to covalently immobilize amino-modified DNA probes which can specifically hybridize with the sequence of at least one specific HLA-A allele, at least one specific HLA-B allele or at least one specific HLA-C allele;
   (d) hybridizing the amplified products with the immobilized DNA probes at 32 to 42° C., wherein the DNA probes are selected depending on the above amplified specific HLA class I gene or group;
   (e) detecting hybridization of the amplified products with the immobilized DNA probes to produce a signal pattern;
   (f) generating a Typing Table using signal patterns obtained by hybridizing the PCR amplified products from samples whose HLA class I antigen types or allele types are known with DNA probes which can specifically hybridize with the sequence of at least one specific HLA class I allele; and (g) determining the type of the HLA class I allele based on the signal pattern detected at step (e) by comparison to the Typing Table.

2. The method according to claim 1, wherein at least one primer of the primer pair is labeled.

3. The method according to claim 2, wherein hybridization of the amplified products with the immobilized DNA probes is determined by the steps of:

(i) adding an enzyme-conjugate which specifically binds to the label of the amplified products thereto at the same time as or after the hybridization, and (ii) adding a chromogenic substrate, a luminescent substrate or a fluorescent substrate to the mixture, so as to detect as signals whether or not the amplified products are hybridized with the immobilized DNA probes.

4. The method according to claim 3, wherein at least one primer of the primer pair is biotinylated and the enzyme-conjugate is an enzyme-conjugated streptavidin.

5. The method according to any one of claims 1 to 4, wherein hybridization occurs at a reaction temperature of about 37° C.

6. The method according to any one of claims 1 to 4, wherein the temperature for washing after hybridization of the amplified products by the PCR method with the immobilized DNA probes and/or after the binding reaction of the label of the amplified products with the enzyme-conjugate is room temperature.

7. The method according to any one of claims 1 to 4, wherein hybridization is performed in the presence of formamide.

8. The method according to claim 7, wherein hybridization occurs at a reaction temperature of about 37° C.

9. The method according to claim 7, wherein the temperature for washing after hybridization of the amplified products by the PCR method with the immobilized DNA probes and/or after the binding reaction of the label of the amplified products with the enzyme-conjugate is room temperature.

10. The method according to claim 7, wherein the concentration of formamide is from 5 to 30%.

11. The method for typing of the HLA class I alleles claimed in claim 1, wherein the amino-modified DNA probe which can specifically hybridize with at least one specific HLA-A allele, at least one specific HLA-B allele or at least one specific HLA-C allele, is A160A (SEQ ID No.:3) or a fully complementary strand thereof.

12. A method for typing HLA class I alleles comprising the steps of:

(a) providing nucleotide sequence(s) encoding HLA class I alleles or a fragment thereof as a template for PCR;

(b) non-selectively amplifying all HLA-A alleles, all HLA-B alleles, or all HLA-C alleles by PCR using a primer pair which can amplify all the HLA-A alleles, all the HLA-B alleles, or all the HLA-C alleles, or selectively amplifying a specific group of HLA-A alleles or a specific group of HLA-B alleles by PCR using a primer pair which is specific to a common nucleotide sequence of the specific group;

(c) adding the resulting PCR products to wells of microtiter plates, which are immobilized DNA probes which can specifically hybridize with the sequence of at least one specific HLA-A allele, at least one specific HLA-B allele or at least one specific HLA-C allele;

(d) hybridizing the amplified products with the immobilized DNA probes at 32 to 42° C., wherein the DNA probes are selected depending on the above amplified specific HLA class I gene or group;

(e) detecting hybridization of the amplified products with the immobilized DNA probes to produce a signal pattern; and (f) generating a Typing Table using signal patterns obtained by hybridizing the PCR amplified products from the samples whose HLA class I antigen types are known with DNA probes which can specifically hybridize with the sequence of at least one specific HLA class I allele; and (g) determining the type of the HLA class I allele based on the signal pattern detected at step (e) according to the Typing Table.

* * * * *

```
                           SEQUENCE LISTING

<160> NUMBER OF SEQ ID NOS: 130

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:DNA probe
      A98T

<400> SEQUENCE: 1
gaggtatttc ttcacatccg tgt                                          23

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:DNA probe
      A98A

<400> SEQUENCE: 2
atgaggtatt tctacacctc cgtgt                                        25

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:DNA probe
      A160A

<400> SEQUENCE: 3
tacgtggaca acacgcagt                                               19

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:DNA probe
      A239A

<400> SEQUENCE: 4
```

```
caggaggagc cggag                                                    15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:DNA probe
      A238A

<400> SEQUENCE: 5
caggagaggc ctgag                                                    15

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:DNA probe
      A240T

<400> SEQUENCE: 6
caggagggtc cggagtat                                                 18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:DNA probe
      A257TC

<400> SEQUENCE: 7
ttgggacctg cagacacg                                                 18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:DNA probe
      A259AC

<400> SEQUENCE: 8
gggaccggaa cacacgg                                                  17

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:DNA probe
      A270T

<400> SEQUENCE: 9
gacacggaat gtgaaggc                                                 18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:DNA probe
      A282C

<400> SEQUENCE: 10
```

```
tgaaggccca ctcacagact                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:DNA probe
      A290T

<400> SEQUENCE: 11
actcacagat tgaccgagtg                                              20

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:DNA probe
      A299T

<400> SEQUENCE: 12
agactgaccg agtggac                                                 17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:DNA probe
      A302G

<400> SEQUENCE: 13
ccgagagagc ctgcgga                                                 17

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:DNA probe
      A355G

<400> SEQUENCE: 14
tctcacaccg tccagagg                                                18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:DNA probe
      A362TA

<400> SEQUENCE: 15
ccgtccagat gatgtatgg                                               19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:DNA probe
      A362TT

<400> SEQUENCE: 16
ccctccagat gatgtttgg                                               19
```

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence:DNA probe
      A368A

<400> SEQUENCE: 17
gaggatgtat ggctgc                                                    16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence:DNA probe
      A368G

<400> SEQUENCE: 18
gaggatgtgt ggctgc                                                    16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence:DNA probe
      A368T

<400> SEQUENCE: 19
gaggatgttt ggctgc                                                    16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence:DNA probe
      A402G

<400> SEQUENCE: 20
cgcttcctgc gcgggt                                                    16

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence:DNA probe
      A423T

<400> SEQUENCE: 21
caggacgctt acgacgg                                                   17

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence:DNA probe
      A448C

<400> SEQUENCE: 22
catcgccctg aacgag                                                    16

```
<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence:DNA probe
      A485A

<400> SEQUENCE: 23
gcggacaagg cagctc                                                          16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence:DNA probe
      A524G

<400> SEQUENCE: 24
gcggcccgtg tggcgg                                                          16

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence:DNA probe
      A526T

<400> SEQUENCE: 25
cggcccgttg ggcggag                                                         17

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence:DNA probe
      A527A

<400> SEQUENCE: 26
gcccatgagg cggag                                                           15

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence:DNA probe
      A538CG

<400> SEQUENCE: 27
gagcagcgga gagtc                                                           15

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence:DNA probe
      A539A

<400> SEQUENCE: 28
gagcagcaga gagcct                                                          16
```

```
<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence:DNA probe
      A539T

<400> SEQUENCE: 29
gagcagttga gagcc                                                        15

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence:DNA probe
      A555T

<400> SEQUENCE: 30
tacctggatg gcacgt                                                       16

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence:DNA probe
      A559G

<400> SEQUENCE: 31
tggagggcga gtgcgt                                                       16

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence:DNA probe
      A570CG

<400> SEQUENCE: 32
gcgtggacgg gctccg                                                       16

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence:DNA probe
      A570GT

<400> SEQUENCE: 33
gcgtggagtg gctcc                                                        15

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence:DNA probe
      A779A

<400> SEQUENCE: 34
caggcctgaa ggggatg                                                      17

<210> SEQ ID NO 35
```

```
<211> LENGTH: 20
<212> TYPE: DNA
<213> ORGANISM: Artificial Sequence
<220> FEATURE:
<223> OTHER INFORMATION: Description of Artificial Sequence:DNA probe
      A843A

<400> SEQUENCE: 35
agcagagata aacctgccat                                              20

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence:DNA probe
      BL1

<400> SEQUENCE: 36
tccgaggaag gagccgc                                                 17

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:DNA probe
      BL3

<400> SEQUENCE: 37
acacggaaca tgaaggcc                                                18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:DNA probe
      BL4

<400> SEQUENCE: 38
acacagatct ccaagacc                                                18

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:DNA probe
      BL5

<400> SEQUENCE: 39
cacagatctt caagaccaa                                               19

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:DNA probe
      BL9

<400> SEQUENCE: 40
gtccgagaga ggagccgc                                                18

<210> SEQ ID NO 41
<211> LENGTH: 18
```

```
<212> TYPE: DNA
<213> ORGANISM: Artificial Sequence
<220> FEATURE:
<223> OTHER INFORMATION: Description of Artificial Sequence:DNA probe
      BL10

<400> SEQUENCE: 41
gatctacaag gcccaggc                                                18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:DNA probe
      BL11

<400> SEQUENCE: 42
gaagtacaag cgccaggc                                                18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence:DNA probe
      BL24

<400> SEQUENCE: 43
ggaccgggag acacagat                                                18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence:DNA probe
      BL25

<400> SEQUENCE: 44
gaccggaaca cacagatc                                                18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:DNA probe
      BL34

<400> SEQUENCE: 45
gcgcggctac tacaacca                                                18

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence:DNA probe
      BL35

<400> SEQUENCE: 46
gctccgctac tacaaccag                                               19

<210> SEQ ID NO 47
<211> LENGTH: 20
<212> TYPE: DNA
```

```
<213> ORGANISM: Artificial Sequence
<220> FEATURE:
<223> OTHER INFORMATION: Description of Artificial Sequence:DNA probe
      BL36

<400> SEQUENCE: 47
ccctccagaa tatgtatggc                                                    20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence:DNA probe
      BL37

<400> SEQUENCE: 48
ctccagagca tgtacggct                                                     19

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:DNA probe
      BL38

<400> SEQUENCE: 49
acaccctcca gaggatgtac                                                    20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:DNA probe
      BL39

<400> SEQUENCE: 50
cgggtctcac atcatccaga                                                    20

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence:DNA probe
      BL40

<400> SEQUENCE: 51
tcacacttgg cagaggat                                                      18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence:DNA probe
      BL41

<400> SEQUENCE: 52
tcacacttgg cagacgat                                                      18

<210> SEQ ID NO 53
<211> LENGTH: 21
<212> TYPE: DNA
<213> ORGANISM: Artificial Sequence
```

```
<220> FEATURE:
<223> OTHER INFORMATION: Description of Artificial Sequence:DNA probe
      BL42

<400> SEQUENCE: 53
acaccctcca gtggatgtat g                                              21

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence:DNA probe
      BL56

<400> SEQUENCE: 54
gcgggcataa ccagtacg                                                  18

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence:DNA probe
      BL57

<400> SEQUENCE: 55
atgaccagtc cgcctacga                                                 19

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence:DNA probe
      BL78

<400> SEQUENCE: 56
tggagggcct gtgcgtg                                                   17

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence:DNA probe
      BL79

<400> SEQUENCE: 57
tggagggcac gtgcgtg                                                   17

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence:DNA probe
      BL222A

<400> SEQUENCE: 58
cgggcgccat ggatagag                                                  18

<210> SEQ ID NO 59
<211> LENGTH: 18
<212> TYPE: DNA
<213> ORGANISM: Artificial Sequence
<220> FEATURE:
```

<223> OTHER INFORMATION: Description of Artificial Sequence:DNA probe
     BL272GA

<400> SEQUENCE: 59
acagatctgc aagaccaa                                              18

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence:DNA probe
     BL226G

<400> SEQUENCE: 60
ccgtgggtgg agcagga                                               17

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:DNA probe
     BL292G

<400> SEQUENCE: 61
gcacagactg accgagag                                              18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence:DNA probe
     BL292T

<400> SEQUENCE: 62
cacagactta ccgagaga                                              18

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:DNA probe
     BL361G

<400> SEQUENCE: 63
atcatccagg tgatgtatgg                                            20

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence:DNA probe
     BL409T

<400> SEQUENCE: 64
ccgcgggtat gaccagt                                               17

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence:DNA probe

```
            BL512T

<400> SEQUENCE: 65
cgcaagttgg aggcg                                                    15

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence:DNA probe
      BL538CG

<400> SEQUENCE: 66
gagcagcgga gagcc                                                    15

<210> SEQ ID NO 67
<211> LENGTH: 17
<212> TYPE: DNA
<213> ORGANISM: Artificial Sequence
<220> FEATURE:
<223> OTHER INFORMATION: Description of Artificial Sequence:DNA probe
      BL538G

<400> SEQUENCE: 67
ggagcaggac agagcct                                                  17

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence:DNA probe
      CC

<400> SEQUENCE: 68
tgggtggagc aggagg                                                   16

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:DNA probe
      A-12

<400> SEQUENCE: 69
catgaagtat ttcttcacat ccgt                                          24

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence:DNA probe
      A-2

<400> SEQUENCE: 70
ctacaccgcc tgtgtcccg                                                19

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence:DNA probe
      A-3
```

```
<400> SEQUENCE: 71
atgaggtatt tctccacatc cg                                          22

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence:DNA probe
      A-4

<400> SEQUENCE: 72
tgaggtattt cgacaccgc                                              19

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence:DNA probe
      A-54

<400> SEQUENCE: 73
gtatttctac accgccgtgt c                                           21

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence:DNA probe
      B-1

<400> SEQUENCE: 74
ccgagtgaac ctgcggaa                                               18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence:DNA probe
      B-2

<400> SEQUENCE: 75
ccgagtgagc ctgcggaa                                               18

<210> SEQ ID NO 76
<211> LENGTH: 15
<212> TYPE: DNA
<213> ORGANISM: Artificial Sequence
<220> FEATURE:
<223> OTHER INFORMATION: Description of Artificial Sequence:DNA probe
      C-12

<400> SEQUENCE: 76
gagcagcgga gagcc                                                  15

<210> SEQ ID NO 77
<211> LENGTH: 14
<212> TYPE: DNA
<213> ORGANISM: Artificial Sequence
<220> FEATURE:
<223> OTHER INFORMATION: Description of Artificial Sequence:DNA probe
      C-24
```

-continued

```
<400> SEQUENCE: 77
gagcagtgga gagc                                                    14

<210> SEQ ID NO 78
<211> LENGTH: 15
<212> TYPE: DNA
<213> ORGANISM: Artificial Sequence
<220> FEATURE:
<223> OTHER INFORMATION: Description of Artificial Sequence:DNA probe
      C-33

<400> SEQUENCE: 78
gagcagctga gagcc                                                   15

<210> SEQ ID NO 79
<211> LENGTH: 15
<212> TYPE: DNA
<213> ORGANISM: Artificial Sequence
<220> FEATURE:
<223> OTHER INFORMATION: Description of Artificial Sequence:DNA probe
      C-43

<400> SEQUENCE: 79
gagcagcaga gagcc                                                   15

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence:DNA probe
      134-g

<400> SEQUENCE: 80
grgagccccg cttcatcg                                                18

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence:DNA probe
      134-A2

<400> SEQUENCE: 81
grgagcccca cttcatcgc                                               19

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence:DNA probe
      353TCA1

<400> SEQUENCE: 82
ggtctcacat catccagagg                                              20

<210> SEQ ID NO 83
<211> LENGTH: 16
<212> TYPE: DNA
<213> ORGANISM: Artificial Sequence
<220> FEATURE:
<223> OTHER INFORMATION: Description of Artificial Sequence:DNA probe
      343A

<400> SEQUENCE: 83
```

-continued cgaggccagt gagtga                                                   16

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence:PCR primer
      A2-5T

<400> SEQUENCE: 84
ctcctcgtcc ccaggctct                                                19

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence:PCR primer
      A3-273T

<400> SEQUENCE: 85
gtggcccctg gtacccgt                                                 18

<210> SEQ ID NO 86
<211> LENGTH: 17
<212> TYPE: DNA
<213> ORGANISM: Artificial Sequence
<220> FEATURE:
<223> OTHER INFORMATION: Description of Artificial Sequence:PCR primer
      A4-8C

<400> SEQUENCE: 86
tccygwcaga csccccc                                                  17

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence:PCR primer
      A4-254G

<400> SEQUENCE: 87
ctcagggtga ggggcttg                                                 18

<210> SEQ ID NO 88
<211> LENGTH: 16
<212> TYPE: DNA
<213> ORGANISM: Artificial Sequence
<220> FEATURE:
<223> OTHER INFORMATION: Description of Artificial Sequence:PCR primer
      BASF-1

<400> SEQUENCE: 88
ccgcgagtcc gaggaa                                                   16

<210> SEQ ID NO 89
<211> LENGTH: 16
<212> TYPE: DNA
<213> ORGANISM: Artificial Sequence
<220> FEATURE:
<223> OTHER INFORMATION: Description of Artificial Sequence:PCR primer
      BASR-1

<400> SEQUENCE: 89
gccactccac gcactc    16

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence:PCR primer
      CGA011

<400> SEQUENCE: 90
ccgaaccctc ctcctgcta    19

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence:PCR primer
      CGA012

<400> SEQUENCE: 91
ccgaaccctc gtcctgcta    19

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence:PCR primer
      AIn3-66C

<400> SEQUENCE: 92
tgttggtccc aattgtctcc cctc    24

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence:PCR primer
      5BIN1-TA

<400> SEQUENCE: 93
ggcgggggcg caggacctga    20

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence:PCR primer
      5BIN1-CG

<400> SEQUENCE: 94
cgggggcgca ggacccgg    18

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence:PCR primer
      3BIN3-37

<400> SEQUENCE: 95
aggccatccc cgscgaccta t    21

-continued

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence:PCR primer
      5BCIn37-34C

<400> SEQUENCE: 96
gagggaaacg gcctctgcgg a                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence:PCR primer
      5BCIn37-24g

<400> SEQUENCE: 97
gagggaagcg gcctctgcgg a                                              21

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence:PCR primer
      3BCIn3-12

<400> SEQUENCE: 98
ggagatgggg aaggctcccc act                                            23

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence:PCR primer
      5BCIn37-34g2

<400> SEQUENCE: 99
tgggagggaa acggcctctg g                                              21

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence:DNA probe
      A34

<400> SEQUENCE: 100
gcgcggctac tacaacca                                                  18

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence:DNA probe
      A282CT

<400> SEQUENCE: 101
tgaaggccca ctcacagatt                                                20

```
<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence:DNA probe
      A290TR

<400> SEQUENCE: 102
actcggtcaa tctgtgagtg                                                   20

<210> SEQ ID NO 103
<211> LENGTH: 17
<212> TYPE: DNA
<213> ORGANISM: Artificial Sequence
<220> FEATURE:
<223> OTHER INFORMATION: Description of Artificial Sequence:DNA probe
      A302GR

<400> SEQUENCE: 103
tccgcaggct ctctcgg                                                      17

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence:DNA probe
      A414A

<400> SEQUENCE: 104
cgggtatgaa cagcacgc                                                     18

<210> SEQ ID NO 105
<211> LENGTH: 16
<212> TYPE: DNA
<213> ORGANISM: Artificial Sequence
<220> FEATURE:
<223> OTHER INFORMATION: Description of Artificial Sequence:DNA probe
      A468T

<400> SEQUENCE: 105
ctgcgctctt ggaccg                                                       16

<210> SEQ ID NO 106
<211> LENGTH: 16
<212> TYPE: DNA
<213> ORGANISM: Artificial Sequence
<220> FEATURE:
<223> OTHER INFORMATION: Description of Artificial Sequence:DNA probe
      A489A

<400> SEQUENCE: 106
gacatggcag ctcaga                                                       16

<210> SEQ ID NO 107
<211> LENGTH: 14
<212> TYPE: DNA
<213> ORGANISM: Artificial Sequence
<220> FEATURE:
<223> OTHER INFORMATION: Description of Artificial Sequence:DNA probe
      A502C

<400> SEQUENCE: 107
atcacccagc gcaa                                                         14
```

<210> SEQ ID NO 108
<211> LENGTH: 15
<212> TYPE: DNA
<213> ORGANISM: Artificial Sequence
<220> FEATURE:
<223> OTHER INFORMATION: Description of Artificial Sequence:DNA probe
      A538TG

<400> SEQUENCE: 108
ggagcagtgg agagc                                                    15

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence:DNA probe
      BL39R

<400> SEQUENCE: 109
ctctggatga tgtgagaccc t                                             21

<210> SEQ ID NO 110
<211> LENGTH: 17
<212> TYPE: DNA
<213> ORGANISM: Artificial Sequence
<220> FEATURE:
<223> OTHER INFORMATION: Description of Artificial Sequence:DNA probe
      BL50

<400> SEQUENCE: 110
gaggatgttt ggctgcg                                                  17

<210> SEQ ID NO 111
<211> LENGTH: 16
<212> TYPE: DNA
<213> ORGANISM: Artificial Sequence
<220> FEATURE:
<223> OTHER INFORMATION: Description of Artificial Sequence:DNA probe
      BL77

<400> SEQUENCE: 111
tggagggcga gtgcgt                                                   16

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence:DNA probe
      BL272A

<400> SEQUENCE: 112
acagatctac aagaccaa                                                 18

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence:DNA probe
      BL263T

<400> SEQUENCE: 113
ccgggagata cagatctc                                                 18

<210> SEQ ID NO 114

```
<211> LENGTH: 15
<212> TYPE: DNA
<213> ORGANISM: Artificial Sequence
<220> FEATURE:
<223> OTHER INFORMATION: Description of Artificial Sequence:DNA probe
      BL527A

<400> SEQUENCE: 114
gcccgtgagg cggag                                               15

<210> SEQ ID NO 115
<211> LENGTH: 15
<212> TYPE: DNA
<213> ORGANISM: Artificial Sequence
<220> FEATURE:
<223> OTHER INFORMATION: Description of Artificial Sequence:DNA probe
      BL570GT

<400> SEQUENCE: 115
gcgtggagtg gctcc                                               15

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence:DNA probe
      RA-2

<400> SEQUENCE: 116
cgggacacag cggtgtag                                            18

<210> SEQ ID NO 117
<211> LENGTH: 17
<212> TYPE: DNA
<213> ORGANISM: Artificial Sequence
<220> FEATURE:
<223> OTHER INFORMATION: Description of Artificial Sequence:DNA probe
      RA-41

<400> SEQUENCE: 117
gcggtgtcga aatacct                                             17

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence:DNA probe
      RB-28

<400> SEQUENCE: 118
caggctcact cggtcagc                                            18

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence:DNA probe
      201g1

<400> SEQUENCE: 119
cgcgagtccg agagggga                                            18

<210> SEQ ID NO 120
<211> LENGTH: 18
```

```
<212> TYPE: DNA
<213> ORGANISM: Artificial Sequence
<220> FEATURE:
<223> OTHER INFORMATION: Description of Artificial Sequence:DNA probe
      C206gR

<400> SEQUENCE: 120
gagtccraga ggggagcc                                                18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence:DNA probe
      R341A

<400> SEQUENCE: 121
actcaccgtc ctcgctct                                                18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence:DNA probe
      R343g3

<400> SEQUENCE: 122
tcactcaccg gcctcgct                                                18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence:DNA probe
      353TCC

<400> SEQUENCE: 123
gtctcacatc ctccagag                                                18

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence:DNA probe
      361T1

<400> SEQUENCE: 124
caccctccag tggatgtatg                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence:DNA probe
      361T368g

<400> SEQUENCE: 125
caccctccag tggatgtgtg                                              20

<210> SEQ ID NO 126
<211> LENGTH: 19
<212> TYPE: DNA
```

```
-continued

<213> ORGANISM: Artificial Sequence
<220> FEATURE:
<223> OTHER INFORMATION: Description of Artificial Sequence:DNA probe
      361T368T1

<400> SEQUENCE: 126
accctccagt ggatgtttg                                                  19

<210> SEQ ID NO 127
<211> LENGTH: 16
<212> TYPE: DNA
<213> ORGANISM: Artificial Sequence
<220> FEATURE:
<223> OTHER INFORMATION: Description of Artificial Sequence:DNA probe
      369C

<400> SEQUENCE: 127
ggatgtacgg ctgcga                                                     16

<210> SEQ ID NO 128
<211> LENGTH: 17
<212> TYPE: DNA
<213> ORGANISM: Artificial Sequence
<220> FEATURE:
<223> OTHER INFORMATION: Description of Artificial Sequence:DNA probe
      387g1

<400> SEQUENCE: 128
ctggggccgg acgggcg                                                    17

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence:DNA probe
      526AC2

<400> SEQUENCE: 129
ggcccgtacg gcgga                                                      15

<210> SEQ ID NO 130
<211> LENGTH: 16
<212> TYPE: DNA
<213> ORGANISM: Artificial Sequence
<220> FEATURE:
<223> OTHER INFORMATION: Description of Artificial Sequence:DNA probe
      538gAC

<400> SEQUENCE: 130
ggagcaggac agagcc                                                     16
```